United States Patent
Bae et al.

(10) Patent No.: US 12,414,980 B2
(45) Date of Patent: Sep. 16, 2025

(54) PHARMACEUTICAL COMPOSITION COMPRISING RUNX3 PROTEIN AND CDK4 INHIBITOR OR mTOR INHIBITOR COTREATMENT FOR PREVENTION OR TREATMENT OF CANCER

(71) Applicant: GeneCraft Inc., Cheongju-si (KR)

(72) Inventors: Suk Chul Bae, Cheongju-si (KR); Jung Won Lee, Daejeon (KR); You Soub Lee, Cheongju-si (KR)

(73) Assignee: GeneCraft, Inc., Cheongju-si (KR)

( * ) Notice: Subject to any disclaimer, the term of this patent is extended or adjusted under 35 U.S.C. 154(b) by 0 days.

(21) Appl. No.: 17/239,433

(22) Filed: Apr. 23, 2021

(65) Prior Publication Data

US 2021/0330742 A1   Oct. 28, 2021

(30) Foreign Application Priority Data

Apr. 23, 2020 (KR) ................. 10-2020-0049341
Dec. 28, 2020 (KR) ................. 10-2020-0184526

(51) Int. Cl.
| | | |
|---|---|---|
| *A61K 38/17* | (2006.01) | |
| *A61K 31/436* | (2006.01) | |
| *A61K 31/519* | (2006.01) | |
| *A61K 47/46* | (2006.01) | |
| *A61P 35/00* | (2006.01) | |
| *C07K 14/47* | (2006.01) | |
| *C12N 7/00* | (2006.01) | |

(52) U.S. Cl.
CPC ............ *A61K 38/17* (2013.01); *A61K 31/436* (2013.01); *A61K 31/519* (2013.01); *A61K 38/1709* (2013.01); *A61K 47/46* (2013.01); *A61P 35/00* (2018.01); *C07K 14/4702* (2013.01); *C12N 7/00* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2008/0261883 A1 | 10/2008 | Bae et al. | |
| 2012/0128642 A1* | 5/2012 | Teumer ............... | G01N 33/6881 435/7.1 |
| 2015/0336967 A1* | 11/2015 | Czardybon .......... | C07D 403/12 540/603 |
| 2018/0002393 A1 | 1/2018 | Bancel et al. | |
| 2021/0330740 A1 | 10/2021 | Bae et al. | |
| 2022/0088126 A1 | 3/2022 | Bae et al. | |

FOREIGN PATENT DOCUMENTS

| | | |
|---|---|---|
| KR | 10-2002-0063387 | 8/2002 |
| KR | 10-1994957 | 6/2019 |
| WO | WO 2013/151672 A2 | 10/2013 |

OTHER PUBLICATIONS

Berns, "Cancer: The blind spot of p53," *Nature* 468.7323: 519-520, Nov. 2010.
Feldser et al., "Stage-specific sensitivity to p53 restoration during lung cancer progression," *Nature* 468.7323: 572-575, Nov. 2010.
Ito et al., "The RUNX family: developmental regulators in cancer," *Nature Reviews Cancer* 15: 81-95, Jan. 2015.
Junttila et al., "Selective activation of p53-mediated tumour suppression in high-grade tumours," *Nature* 468.7323: 567-571, Nov. 2010.
Lee et al., "Runx3 is required for the differentiation of lung epithelial cells and suppression of lung cancer," *Oncogene* 29: 3349-3361, Mar. 2010.
Lee et al., "Runx3 Inactivation is a Crucial Early Event in the Development of Lung Adenocarcinoma," *Cancer Cell* 24: 603-616, Nov. 2013.
Lee et al., "RUNX3 protects against oncogenic KRAS," *Cancer Discovery* 4.1: 14, Jan. 2014.
Lee et al., "RUNX3 regulates cell cycle-dependent chromatin dynamics by functioning as a pioneer factor of the restriction-point," *Nat Commun.* 10: 1897, 2019 (17 pages).
"Study on the decision making mechanism for cell division," Final (Result) Report of Research Fellow for Academic Successor Generation Project, 2017 (w/English translation of summary of research results).
Walter et al., "RB constrains lineage fidelity and multiple stages of tumour progression and metastasis," *Nature* 569.7756: 423-427, May 2019 (w/supplemental information).
Wang et al., "Comparison of Adenoviral and Adeno-Associated Viral Vectors for Pancreatic Gene Delivery In Vivo," *Hum Gene Ther.* 15.4: 405-413, Apr. 2004.

(Continued)

*Primary Examiner* — Maury A Audet
(74) *Attorney, Agent, or Firm* — Klarquist Sparkman, LLP

(57) ABSTRACT

The present invention relates to a pharmaceutical composition for prevention or treatment of cancer, comprising a Runx3 (Runt-related transcription factor 3) protein, a polynucleotide encoding thereof, a vector carrying the polynucleotide or a virus or cell transformed with the vector; and a CDK4 inhibitor or an mTOR inhibitor as an active ingredient. It was confirmed that the binding of Runx3 and BRD2 was maintained for up to 8 hours when the CDK4 inhibitor (PD0332991) was present at the concentration of 11 nM known to be non-toxic to normal cells. It was also confirmed that the binding of Runx3 and BRD2 was maintained for up to 8 hours when the mTOR inhibitor (rapamycin) was present at the concentration of 100 nM known to be non-cytotoxic to normal cells. In addition, it was confirmed that the cancer apoptotic effect was significantly increased when the CDK4 inhibitor or mTOR inhibitor was administered simultaneously with Runx3 than when Runx3 was administered alone to Runx3 deficient cancer cells. Therefore, the CDK4 inhibitor or mTOR inhibitor can be effectively used for preventing or treating various cancers by administering the same in combination with Runx3.

6 Claims, 21 Drawing Sheets

Specification includes a Sequence Listing.

(56) References Cited

OTHER PUBLICATIONS

Wang et al., "Targeting adeno-associated virus and adenoviral gene therapy for hepatocellular carcinoma," *World J Gastroenterol.* 22.1: 326-337, Jan. 2016.

El-Aneed, Anas, "An overview of current delivery systems in cancer gene therapy," *Journal of Controlled Release,* vol. 94, pp. 1-14, 2004.

Strausberg et al., "Generation and initial analysis of more than 15,000 full-length human and mouse cDNA sequences," *PNAS,* vol. 99, No. 26, pp. 16899-16903, 2002.

Mukhopadhyay et al., "The Enigma of Rapamycin Dosage," *Molecular Cancer Therapeutics,* 15(3): 347-353, 2016.

Xue et al., "Therapeutic evaluation of palbociclib and its compatibility with other chemotherapies for primary and recurrent nasopharyngeal carcinoma," *Journal of Experimental & Clinical Cancer Research,* 39: Article 262, 2020 (24 pages).

Zhang et al., "PTHrP prevents chondrocyte premature hypertrophy by inducing cyclin-D1-dependent Runx2 and Runx3 phosphorylation, ubiquitylation and proteasomal degradation," *J Cell Sci,* vol. 122 (Pt. 9), pp. 1382-1389, 2009.

Kemp et al., "Elimination of background recombination: somatic induction of Cre by combined transcriptional regulation and hormone binding affinity," *Nucleic Acids Research* 32.11: e92, Jul. 2004 (7 pages).

Kudo et al., "Oncogenic Role of RUNX3 in Head and Neck Cancer," *J Cell. Biol.* 112: 387-393, 2011.

Lee et al., "RUNX3 functions as an oncogene in ovarian cancer," *Gynecologic Oncology* 122: 410-417, May 2011.

Stolze et al., "Comparative analysis of KRAS codon 12, 13, 18,61, and 117 mutations using human MCFIOA isogenic cell lines," *Scientific Reports* 5: 8535, Feb. 2015 (9 pages).

\* cited by examiner

MKN28 cells

SEQUENCE LISTING

```
<160> NUMBER OF SEQ ID NOS: 14

<210> SEQ ID NO 1
<211> LENGTH: 19
<212> TYPE: RNA
<213> ORGANISM: Artificial Sequence
<220> FEATURE:
<223> OTHER INFORMATION: si-BRD2 sense

<400> SEQUENCE: 1
cacuuggccu gcaugacua                                              19

<210> SEQ ID NO 2
<211> LENGTH: 19
<212> TYPE: RNA
<213> ORGANISM: Artificial Sequence
<220> FEATURE:
<223> OTHER INFORMATION: si-BRD2 anti-sense

<400> SEQUENCE: 2
uagucaugca ggccaagug                                              19

<210> SEQ ID NO 3
<211> LENGTH: 18
<212> TYPE: RNA
<213> ORGANISM: Artificial Sequence
<220> FEATURE:
<223> OTHER INFORMATION: si-p53 sense
```

```
<400> SEQUENCE: 3
caguuugagg ugcguguu                                                  18

<210> SEQ ID NO 4
<211> LENGTH: 19
<212> TYPE: RNA
<213> ORGANISM: Artificial Sequence
<220> FEATURE:
<223> OTHER INFORMATION: si-p53 anti-sense

<400> SEQUENCE: 4
aacacgcacc ucaaagcug                                                 19

<210> SEQ ID NO 5
<211> LENGTH: 19
<212> TYPE: RNA
<213> ORGANISM: Artificial Sequence
<220> FEATURE:
<223> OTHER INFORMATION: si-CDK4 sense

<400> SEQUENCE: 5
ccagaaucua cagcuacca                                                 19

<210> SEQ ID NO 6
<211> LENGTH: 20
<212> TYPE: RNA
<213> ORGANISM: Artificial Sequence
<220> FEATURE:
<223> OTHER INFORMATION: si-CDK4 anti-sense

<400> SEQUENCE: 6
ugguagcugu agauuccugg                                                20

<210> SEQ ID NO 7
<211> LENGTH: 19
<212> TYPE: RNA
<213> ORGANISM: Artificial Sequence
<220> FEATURE:
<223> OTHER INFORMATION: si-Cyclin D1 sense

<400> SEQUENCE: 7
gaccuucguu gcccucugu                                                 19

<210> SEQ ID NO 8
<211> LENGTH: 19
<212> TYPE: RNA
<213> ORGANISM: Artificial Sequence
<220> FEATURE:
<223> OTHER INFORMATION: si-Cyclin D1 anti-sense

<400> SEQUENCE: 8
acagagggca acgaagguc                                                 19

<210> SEQ ID NO 9
<211> LENGTH: 19
<212> TYPE: RNA
<213> ORGANISM: Artificial Sequence
<220> FEATURE:
<223> OTHER INFORMATION: si-RNF2 sense

<400> SEQUENCE: 9
ugauagggua uugagugua                                                 19

<210> SEQ ID NO 10
<211> LENGTH: 19
```

```
<212> TYPE: RNA
<213> ORGANISM: Artificial Sequence
<220> FEATURE:
<223> OTHER INFORMATION: si-RNF2 anti-sense

<400> SEQUENCE: 10
uacacucaau acccuauca                                                      19

<210> SEQ ID NO 11
<211> LENGTH: 429
<212> TYPE: PRT
<213> ORGANISM: Artificial Sequence
<220> FEATURE:
<223> OTHER INFORMATION: Runx3 isoform1 amino acid

<400> SEQUENCE: 11
```

Met Ala Ser Asn Ser Ile Phe Asp Ser Phe Pro Thr Tyr Ser Pro Thr
 1               5                  10                  15

Phe Ile Arg Asp Pro Ser Thr Ser Arg Arg Phe Thr Pro Pro Ser Pro
             20                  25                  30

Ala Phe Pro Cys Gly Gly Gly Gly Lys Met Gly Glu Asn Ser Gly
         35                  40                  45

Ala Leu Ser Ala Gln Ala Ala Val Gly Pro Gly Gly Arg Ala Arg Pro
     50                  55                  60

Glu Val Arg Ser Met Val Asp Val Leu Ala Asp His Ala Gly Glu Leu
65                  70                  75                  80

Val Arg Thr Asp Ser Pro Asn Phe Leu Cys Ser Val Leu Pro Ser His
                 85                  90                  95

Trp Arg Cys Asn Lys Thr Leu Pro Val Ala Phe Lys Val Val Ala Leu
            100                 105                 110

Gly Asp Val Pro Asp Gly Thr Val Val Thr Val Met Ala Gly Asn Asp
        115                 120                 125

Glu Asn Tyr Ser Ala Glu Leu Arg Asn Ala Ser Ala Val Met Lys Asn
    130                 135                 140

Gln Val Ala Arg Phe Asn Asp Leu Arg Phe Val Gly Arg Ser Gly Arg
145                 150                 155                 160

Gly Lys Ser Phe Thr Leu Thr Ile Thr Val Phe Thr Asn Pro Thr Gln
                165                 170                 175

Val Ala Thr Tyr His Arg Ala Ile Lys Val Thr Val Asp Gly Pro Arg
            180                 185                 190

Glu Pro Arg Arg His Arg Gln Lys Leu Glu Asp Gln Thr Lys Pro Phe
        195                 200                 205

Pro Asp Arg Phe Gly Asp Leu Glu Arg Leu Arg Met Arg Val Thr Pro
    210                 215                 220

Ser Thr Pro Ser Pro Arg Gly Ser Leu Ser Thr Thr Ser His Phe Ser
225                 230                 235                 240

Ser Gln Pro Gln Thr Pro Ile Gln Gly Thr Ser Glu Leu Asn Pro Phe
                245                 250                 255

Ser Asp Pro Arg Gln Phe Asp Arg Ser Phe Pro Thr Leu Pro Thr Leu
            260                 265                 270

Thr Glu Ser Arg Phe Pro Asp Pro Arg Met His Tyr Pro Gly Ala Met
        275                 280                 285

Ser Ala Ala Phe Pro Tyr Ser Ala Thr Pro Ser Gly Thr Ser Ile Ser
    290                 295                 300

Ser Leu Ser Val Ala Gly Met Pro Ala Thr Ser Arg Phe His His Thr
305                 310                 315                 320

```
Tyr Leu Pro Pro Pro Tyr Pro Gly Ala Pro Gln Asn Gln Ser Gly Pro
            325                 330                 335

Phe Gln Ala Asn Pro Ser Pro Tyr His Leu Tyr Gly Thr Ser Ser
            340                 345                 350

Gly Ser Tyr Gln Phe Ser Met Val Ala Gly Ser Ser Ser Gly Gly Asp
            355                 360                 365

Arg Ser Pro Thr Arg Met Leu Ala Ser Cys Thr Ser Ser Ala Ala Ser
370                 375                 380

Val Ala Ala Gly Asn Leu Met Asn Pro Ser Leu Gly Gly Gln Ser Asp
385                 390                 395                 400

Gly Val Glu Ala Asp Gly Ser His Ser Asn Ser Pro Thr Ala Leu Ser
            405                 410                 415

Thr Pro Gly Arg Met Asp Glu Ala Val Trp Arg Pro Tyr
            420                 425

<210> SEQ ID NO 12
<211> LENGTH: 415
<212> TYPE: PRT
<213> ORGANISM: Artificial Sequence
<220> FEATURE:
<223> OTHER INFORMATION: Runx3 isoform2 amino acid

<400> SEQUENCE: 12

Met Arg Ile Pro Val Asp Pro Ser Thr Ser Arg Arg Phe Thr Pro Pro
1               5                   10                  15

Ser Pro Ala Phe Pro Cys Gly Gly Gly Gly Lys Met Gly Glu Asn
            20                  25                  30

Ser Gly Ala Leu Ser Ala Gln Ala Val Gly Pro Gly Gly Arg Ala
            35                  40                  45

Arg Pro Glu Val Arg Ser Met Val Asp Val Leu Ala Asp His Ala Gly
50                  55                  60

Glu Leu Val Arg Thr Asp Ser Pro Asn Phe Leu Cys Ser Val Leu Pro
65                  70                  75                  80

Ser His Trp Arg Cys Asn Lys Thr Leu Pro Val Ala Phe Lys Val Val
            85                  90                  95

Ala Leu Gly Asp Val Pro Asp Gly Thr Val Val Thr Val Met Ala Gly
            100                 105                 110

Asn Asp Glu Asn Tyr Ser Ala Glu Leu Arg Asn Ala Ser Ala Val Met
            115                 120                 125

Lys Asn Gln Val Ala Arg Phe Asn Asp Leu Arg Phe Val Gly Arg Ser
            130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
            165                 170                 175

Pro Arg Glu Pro Arg Arg His Arg Gln Lys Leu Glu Asp Gln Thr Lys
            180                 185                 190

Pro Phe Pro Asp Arg Phe Gly Asp Leu Glu Arg Leu Arg Met Arg Val
            195                 200                 205

Thr Pro Ser Thr Pro Ser Pro Arg Gly Ser Leu Ser Thr Thr Ser His
            210                 215                 220

Phe Ser Ser Gln Pro Gln Thr Pro Ile Gln Gly Thr Ser Glu Leu Asn
225                 230                 235                 240

Pro Phe Ser Asp Pro Arg Gln Phe Asp Arg Ser Phe Pro Thr Leu Pro
            245                 250                 255
```

Thr Leu Thr Glu Ser Arg Phe Pro Asp Pro Arg Met His Tyr Pro Gly
                260                 265                 270

Ala Met Ser Ala Ala Phe Pro Tyr Ser Ala Thr Pro Ser Gly Thr Ser
            275                 280                 285

Ile Ser Ser Leu Ser Val Ala Gly Met Pro Ala Thr Ser Arg Phe His
        290                 295                 300

His Thr Tyr Leu Pro Pro Pro Tyr Pro Gly Ala Pro Gln Asn Gln Ser
305                 310                 315                 320

Gly Pro Phe Gln Ala Asn Pro Ser Pro Tyr His Leu Tyr Tyr Gly Thr
                325                 330                 335

Ser Ser Gly Ser Tyr Gln Phe Ser Met Val Ala Gly Ser Ser Ser Gly
            340                 345                 350

Gly Asp Arg Ser Pro Thr Arg Met Leu Ala Ser Cys Thr Ser Ser Ala
        355                 360                 365

Ala Ser Val Ala Ala Gly Asn Leu Met Asn Pro Ser Leu Gly Gly Gln
    370                 375                 380

Ser Asp Gly Val Glu Ala Asp Gly Ser His Ser Asn Ser Pro Thr Ala
385                 390                 395                 400

Leu Ser Thr Pro Gly Arg Met Asp Glu Ala Val Trp Arg Pro Tyr
                405                 410                 415

<210> SEQ ID NO 13
<211> LENGTH: 1380
<212> TYPE: DNA
<213> ORGANISM: Artificial Sequence
<220> FEATURE:
<223> OTHER INFORMATION: Runx3 isoform1 polynucleotide

<400> SEQUENCE: 13
gccttcttca gagcggggca tggcatcgaa cagcatcttc gactccttcc cgacctactc    60
gccgaccttc atccgcgacc caagcaccag ccgccgcttc acacctccct ccccggcctt   120
cccctgcggc ggcggcggcg gcaagatggg cgagaacagc ggcgcgctga gcgcgcaggc   180
ggccgtgggg cccggagggc gcgcccggcc cgaggtgcgc tcgatggtgg acgtgctggc   240
ggaccacgca ggcgagctcg tgcgcaccga cagccccaac ttcctctgct ccgtgctgcc   300
ctcgcactgg cgctgcaaca gacgctgccg cgtcgccttc aaggtggtgg cattggggga   360
cgtgccggat ggtacggtgg tgactgtgat ggcaggcaat gacgagaact actccgctga   420
gctgcgcaat gcctcggccg tcatgaagaa ccaggtggcc aggttcaacg accttcgctt   480
cgtgggccgc agtgggcgag ggaagagttt caccctgacc atcactgtgt tcaccaaccc   540
cacccaagtg gcgacctacc accgagccat caaggtgacc gtggacggac cccgggagcc   600
cagacggcac cggcagaagc tggaggacca gaccaagccg ttccctgacc gctttgggga   660
cctggaacgg ctgcgcatgc gggtgacacc gagcacaccc agccccgag gctcactcag   720
caccacaagc cacttcagca gccagcccca gaccccaatc caaggcacct cggaactgaa   780
cccattctcc gaccccgcc agtttgaccg ctccttcccc acgctgccaa ccctcacgga   840
gagccgcttc ccagacccca ggatgcatta tccggggcc atgtcagctg ccttccccta   900
cagcgccacg ccctcgggca cgagcatcag cagcctcagc gtggcgggca tgccggccac   960
cagccgcttc caccatacct acctcccgcc acctacccg ggggccccgc agaaccagag  1020
cgggcccttc caggcaacc cgtcccccta ccacctctac tacgggacat cctctggctc  1080
ctaccagttc tccatggtgg ccggcagcag cagtgggggc gaccgctcac ctaccccgcat  1140
gctggcctct tgcaccagca gcgctgcctc tgtcgccgcc ggcaacctca tgaaccccag  1200

```
cctgggcggc cagagtgatg gcgtggaggc cgacggcagc cacagcaact cacccacggc    1260
cctgagcacg ccaggccgca tggatgaggc cgtgtggcgg ccctactgac cgccctggtg    1320
gactcctccc gctggaggcg gggaccctaa caaccttcaa gaccagtgat gggccggctc    1380

<210> SEQ ID NO 14
<211> LENGTH: 1320
<212> TYPE: DNA
<213> ORGANISM: Artificial Sequence
<220> FEATURE:
<223> OTHER INFORMATION: Runx3 isoform2 polynucleotide

<400> SEQUENCE: 14
cgggggaagc cgcgccgtct ccgcctgccc ggcgccctga cggccgctgt tatgcgtatt      60
cccgtagacc caagcaccag ccgccgcttc acacctccct ccccggcctt ccctgcggc     120 ggcggcggcg gcaagatggg cgagaacagc ggcgcgctga gcgcgcaggc ggccgtgggg    180
cccggagggc gcgcccggcc cgaggtgcgc tcgatggtgg acgtgctggc ggaccacgca    240
ggcgagctcg tgcgcaccga cagccccaac ttcctctgct ccgtgctgcc ctcgcactgg    300
cgctgcaaca agacgctgcc cgtcgccttc aaggtggtgg cattgggggga cgtgccggat    360 ggtacggtgg tgactgtgat ggcaggcaat gacgagaact actccgctga gctgcgcaat    420
gcctcggccc tcatgaagaa ccaggtggcc aggttcaacg accttcgctt cgtgggccgc    480
agtgggcgag ggaagagttt cacccctgacc atcactgtgt tcaccaaccc cacccaagtg    540
gcgacctacc accgagccat caaggtgacc gtggacggac cccggagcc cagacggcac    600 cggcagaagc tggaggacca gaccaagccg ttccctgacc gctttgggga cctggaacgg    660
ctgcgcatgc gggtgacacc gagcacaccc agccccgag gctcactcag caccacaagc    720
cacttcagca gccagcccca gacccccaatc caaggcacct cggaactgaa cccattctcc    780
gacccccgcc agtttgaccg ctccttcccc acgctgccaa ccctcacgga gagccgcttc    840
ccagacccca ggatgcatta tcccggggcc atgtcagctg ccttccccta cagcgccacg    900
ccctcgggca cgagcatcag cagcctcagc gtggcgggca tgccggccac cagccgcttc    960 caccataacct acctcccgcc accctacccg ggggccccgc agaaccagag cgggcccttc   1020
caggccaacc cgtcccccta ccacctctac tacgggacat cctctggctc ctaccagttc   1080
tccatggtgg ccggcagcag cagtggggggc gaccgctcac ctaccgcat gctggcctct   1140 tgcaccagca gcgctgcctc tgtcgccgcc ggcaacctca tgaacccag cctgggcggc   1200 cagagtgatg gcgtggaggc cgacggcagc cacagcaact cacccacggc cctgagcacg   1260
ccaggccgca tggatgaggc cgtgtggcgg ccctactgac cgccctggtg gactcctccc   1320
```

PHARMACEUTICAL COMPOSITION COMPRISING RUNX3 PROTEIN AND CDK4 INHIBITOR OR mTOR INHIBITOR COTREATMENT FOR PREVENTION OR TREATMENT OF CANCER

CROSS REFERENCE TO RELATED APPLICATIONS

This application claims the benefit of priority from Korean Patent Application No. 10-2020-0049341, filed on Apr. 23, 2020, and Korean Patent Application No. 10-2020-0184526, filed on Dec. 28, 2020, the contents of each of which are incorporated herein by reference.

BACKGROUND OF THE INVENTION

1. Field of the Invention

The present invention relates to a pharmaceutical composition comprising a Runx3 protein and a CDK4 inhibitor or an mTOR inhibitor as an active ingredient.

2. Description of the Related Art

Research on the development of targeted cancer therapy is focused on strategies to control cancer cells by inhibiting the function of an oncogene or activating the function of a tumor suppressor gene. Abnormal activation of K-Ras function by mutation of K-Ras among the oncogenes is known as one of the major causes of human cancer. The mutation of K-Ras is also observed in lung cancer, and it is known that the mutation of K-Ras is observed in about 35% of lung adenocarcinoma. Thus, in order to treat cancer caused by the activation of K-Ras function, studies have been conducted on a method of treating cancer by inhibiting the function of K-Ras. However, a strategy that directly inhibits the function of K-Ras has not been developed as a successful anticancer drug because it causes serious damage to normal cells. Therefore, instead of suppressing the function of an oncogene, a strategy of activating the inhibited function of a tumor suppressor gene is receiving attention. Therefore, instead of a strategy for inhibiting the function of an oncogene, a strategy for activating the inhibited function of a tumor suppressor gene is attracting attention.

The said tumor suppressor gene refers to a nucleotide sequence that can be expressed in a target cell to suppress a tumor phenotype or induce apoptosis. The tumor suppressor genes identified so far include sPD-1, VHL, MMAC1, DCC, p53, NF1, WT1, Rb, BRCA1 and BRCA2. Among them, it has been reported that p53 or Rb gene is frequently inhibited in its function in K-Ras mutant cancers. Whether it is possible to treat K-Ras mutant cancer through the repair of the suppressor gene has become a subject of great interest in the field of anticancer agent development research. Accordingly, there have been attempts to treat K-Ras mutant lung adenocarcinoma by recovering the function of p53 gene, which is a representative tumor suppressor gene, but it was not successful because early lung adenocarcinoma was not cured (Feldser, D. M. et al., Nature, 468: 572-575, 2010, Junttila, M. R. et al., Nature, 468: 567-571, 2010). In addition, it was found that K-Ras mutant lung cancer could not be cured through the recovery of Rb gene function (Walter, D. M. et al. Nature 2019). The above results indicate that even if the function of the tumor suppressor gene is simply restored, the therapeutic effect on the already-onset cancer does not appear, because the early stage cancer rapidly develops into a malignant cancer (Berns A., Nature, 468:519-520, 2010). There have been no reports of successful treatment of K-Ras mutant lung cancer through the activation of a tumor suppressor gene.

It has been reported that the function of Runx3 gene as a tumor suppressor gene is inhibited in K-Ras mutant cancers (RUNX3 Protects against Oncogenic KRAS. (2013). Cancer Discovery, 4(1), 14-14), and that the activity of Runx3 gene is inhibited in lung adenocarcinoma caused by the mutation of K-Ras (Lee, K. S., Lee, Y. S., Lee, J. M., Ito, K., Cinghu, S., Kim, J. H., Bae, S. C. Oncogene, 29(23): 3349-61, 2010).

Runx3, a transcription factor that binds to DNA, plays a crucial role in lineage determination (Ito, Y., Bae, S. C. & Chuang, L. S. The RUNX family: developmental regulators in cancer. Nat. Rev. Cancer 15, 81-95 (2015)). Deletion of Runx3 in the mouse lung leads to the development of lung adenomas and accelerates the progression to adenocarcinoma (ADCs) induced by K-Ras.

Thus, the present inventors have completed the present invention by confirming that the cancer apoptotic effect was significantly increased when the CDK4 inhibitor or mTOR inhibitor was administered simultaneously with Runx3 protein compared to when Runx3 was introduced alone into Runx3 deficient cancer cells since the CDK4 inhibitor and mTOR inhibitor increased the time for maintaining the Runx3-BRD2 complex.

SUMMARY OF THE INVENTION

It is an object of the present invention to provide a pharmaceutical composition for prevention or treatment of cancer.

To achieve the above object, the present invention provides a pharmaceutical composition for prevention or treatment of cancer, comprising a modified protein in which the $356^{th}$ serine of Runx3 (Runt-related transcription factor 3) protein is substituted with a hydrophobic amino acid, a polynucleotide encoding thereof, a vector carrying the polynucleotide, or a virus or cell transformed with the vector as an active ingredient.

The present invention also provides a pharmaceutical composition for prevention or treatment of cancer, comprising a Runx3 (Runt-related transcription factor 3) protein, a polynucleotide encoding thereof, a vector carrying the polynucleotide or a virus or cell transformed with the vector; and a CDK4 inhibitor as an active ingredient.

In addition, the present invention provides a pharmaceutical composition for prevention or treatment of cancer, comprising a Runx3 (Runt-related transcription factor 3) protein, a polynucleotide encoding thereof, a vector carrying the polynucleotide or a virus or cell transformed with the vector; and an mTOR inhibitor as an active ingredient.

Advantageous Effect

The present invention relates to a pharmaceutical composition for prevention or treatment of cancer, comprising a Runx3 (Runt-related transcription factor 3) protein, a polynucleotide encoding thereof, a vector carrying the polynucleotide or a virus or cell transformed with the vector; and a CDK4 inhibitor or an mTOR inhibitor as an active ingredient. It was confirmed that the binding of Runx3 and BRD2 was maintained for up to 8 hours when the CDK4 inhibitor (PD0332991) was present at the concentration of 11 nM known to be non-toxic to normal cells. It was also confirmed that the binding of Runx3 and BRD2 was maintained for up to 8 hours when the mTOR inhibitor (rapamycin) was present at the concentration of 100 nM known to be non-toxic to normal cells. In addition, it was confirmed that the cancer apoptotic effect was significantly increased when the CDK4 inhibitor or mTOR inhibitor was administered simultaneously with Runx3 than when Runx3 was administered alone to Runx3 deficient cancer cells. Therefore, the CDK4 inhibitor or mTOR inhibitor can be effectively used for preventing or treating various cancers by administering the same in combination with Runx3.

SEQUENCE

Figure 1A:
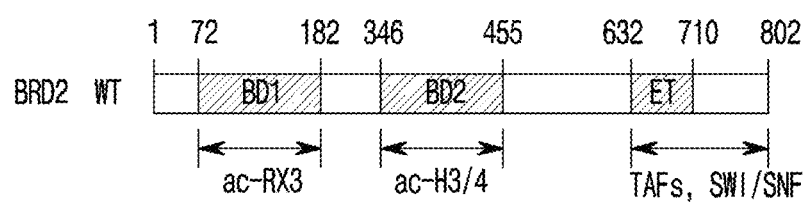
FIG. 1a is a schematic diagram illustrating the BRD2 structure and the interacting proteins, confirming that BD1 interacted with the RUNX3 acetylated at Lys-94 and Lys-171, BD2 interacted with the acetylated histones H4K4-ac, H4K12-ac and H3K14-ac, and C-terminal region interacted with TFIID and SWI/SNF complex.

The Sequence Listing is submitted as an ASCII text file in the form of the file name "Sequence.txt" (~13 kb), which was created on Apr. 22, 2021, and which is incorporated by reference herein.

DESCRIPTION OF THE PREFERRED EMBODIMENTS

Hereinafter, the present invention is described in detail.

The present invention provides a pharmaceutical composition for prevention or treatment of cancer, comprising a Runx3 (Runt-related transcription factor 3) protein, a polynucleotide encoding thereof, a vector carrying the polynucleotide or a virus or cell transformed with the vector; and a CDK4 inhibitor as an active ingredient.

The CDK4 inhibitor can be any one selected from the group consisting of Abemaciclib, Palbociclib and Ribociclib, but not always limited thereto.

The CDK4 inhibitor is represented by the following formula 1.

[Formula 1]

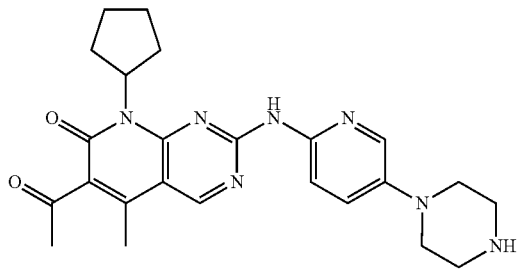

The present invention also provides a pharmaceutical composition for prevention or treatment of cancer, comprising a Runx3 (Runt-related transcription factor 3) protein, a polynucleotide encoding thereof, a vector carrying the polynucleotide or a virus or cell transformed with the vector; and an mTOR inhibitor as an active ingredient.

The mTOR inhibitor can be any one selected from the group consisting of rapamycin, Ridaforolimus, Everolimus and Temsirolimus, but not always limited thereto.

The mTOR inhibitor is represented by the following formula 2.

[Formula 2]

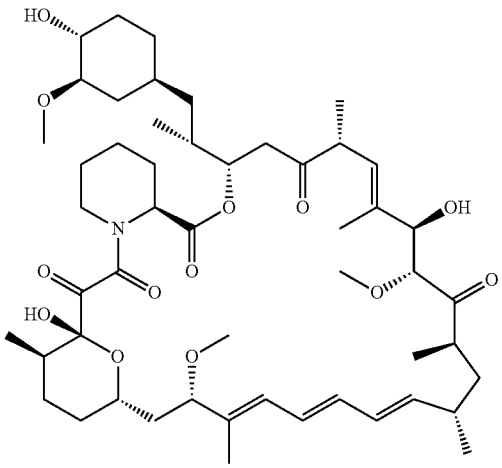

The cancer is solid cancer.

The solid cancer can be one or more selected from the group consisting of lung cancer, pancreatic cancer, liver cancer and stomach cancer, but not always limited thereto.

Runx3 (Runt-related transcription factor 3) gene is one of the Runt family genes consisting of Runx1, Runx2 and Runx3. The Runt family genes play an important role in normal development and oncogenesis, and they function as transcriptional regulators of the Smad family, a downstream factor that mediates TGF-β and its signaling. Runx1 plays an important role in mammalian hematopoiesis, Runx2 plays an important role in bone formation, and Runx3 is mainly expressed in granular gastric mucosal cells, and plays a role in inhibiting cell differentiation of gastric epithelium. These three genes are located at loci of chromosomes 1p, 6p and 21q, of which Runx3 gene is located at 1p36. 11-1p36. 13. The Runx3 locus is one of the sites that are lost in a variety of cancers or affected by hemizygous defects. In addition, Runx3 has been found to be inactivated in various types of cancer, and it is gaining spotlight as a new target for the development of anticancer agents. As such, Runx3 is known to act as a tumor suppressor gene that suppresses the formation of cancer, and plays an important role in the restriction-point, which determines the fate of cell division and death, and induces cell division or apoptosis depending on the situation (Lee et al., Nat Commun. 2019; 10(1): RUNX3 regulates cell cycle-dependent chromatin dynamics by functioning as a pioneer factor of the restriction-point). When a K-Ras oncogene mutation occurs in lung epithelial cells, Runx3 kills cancer cells by contributing to determining apoptosis fate at the restriction-point (Lee et al., Nat Commun. 2019; 10(1)).

A Runx3 protein refers to a Runt-related transcription factor 3 related to the Runt family expressed by the Runx3 gene.

BRD2 (bromodomain-containing protein 2) is a factor that acts as a signaling mediator in the nucleus. It is widely expressed in mammalian cells, and plays an important role in cell cycle regulation and transcriptional regulation.

The said BRD2 binds to the acetylated Runx3 to form Runx3-Brd2 complex.

The bromodomain 1 (BD1) of the BRD2 binds to the lysine residues 94 and 171 of Runx3.

The bromodomain 2 (BD2) of the BRD2 binds to the lysine residue 5 of the acetylated histone 4 of Runx3, the lysine residue 12 of histone 4, and the lysine residue 14 of histone 3.

The CDK4 inhibitor or mTOR inhibitor increases the time for maintaining the Runx3-Brd2 complex.

The Runx3-Brd2 complex is formed by mitogenic stimulation, and contributes to the determination of restriction point (R-point).

The restriction point (R-point) is a step in the cell division process that allows cells to make their own decisions to continue life or die. Normal cells make decisions about life by themselves and divide, but abnormal cells such as cancer cells decide to kill themselves at this R-point, thereby removing mutant cells from the body and maintaining normal cells.

The Runx3 protein can be composed of the amino acid sequence represented by SEQ. ID. NO: 11 or SEQ. ID. NO: 12.

The Runx3 protein can be derived from humans or animals.

The Runx3 protein can be synthesized by the conventional chemical synthesis method in the art (W.H. Freeman and Co., Proteins; structures and molecular principles, 1983), or can be prepared by the conventional genetic engineering method (Maniatis et al., Molecular Cloning: A laboratory Manual, Cold Spring Harbor laboratory, 1982; Sambrook et al., Molecular Cloning: A Laboratory Manual et al.).

The Runx3 protein can be a variant of an amino acid sequence having a different sequence by deletion, insertion or substitution of amino acid residues, or a combination thereof within a range that does not affect the function of the protein. Amino acid exchanges in proteins that do not totally alter the activity of the molecule are informed in the art. In some cases, the amino acid can be modified by phosphorylation, sulfation, acrylation, glycosylation, methylation or farnesylation. Accordingly, the present invention can include a peptide having an amino acid sequence substantially identical to that of a protein composed of the amino acid sequence represented by SEQ. ID. NO: 1 or SEQ. ID. NO: 2, and variants or fragments thereof. The substantially identical protein can have homology to the protein of the present invention by 80% or more, particularly 90% or more, and more particularly 95% or more.

The polynucleotide encoding the Runx3 protein can be derived from humans or animals.

The polynucleotide encoding the Runx3 protein can be composed of the nucleotide sequence represented by SEQ. ID. NO: 13 or SEQ. ID. NO: 14.

The vector including the polynucleotide encoding the Runx3 protein can be linear DNA or plasmid DNA.

The vector refers to a transport mediator for introducing the polynucleotide encoding the Runx3 protein of the present invention into a subject to be treated, and can include a promoter suitable for expression in a subject to be treated, an enhancer, and a polynucleotide encoding the Runx3 protein, a transcription termination site, and the like. The promoter can be a specific organ and tissue specific promoter, and can include a replication origin so as to proliferate in the organ and tissue.

The virus transformed by the vector can be any one selected from the group consisting of retrovirus, adenovirus, herpes simplex virus and lentivirus, but not always limited thereto.

In the case of the vector containing the polynucleotide, it is preferably to contain 0.05 to 500 mg, and more preferably to contain 0.1 to 300 mg. In the case of the recombinant virus containing the polynucleotide encoding Runx3 protein, it is preferably to contain $10^3$ to $10^{12}$ IU (10 to $10^{10}$ PFU), and more preferably to contain $10^5$ to $10^{10}$ IU.

The recombinant virus is preferably adenovirus. Adeno-associated virus (AAV) is unsuitable as a delivery vehicle for cancer treatment because its gene expression rate or expression speed is lower than that of adenovirus. Adenovirus is suitable for the delivery of the modified protein according to the present invention to the human body because the transferred gene is expressed in adenovirus more than 3 weeks faster than in adeno-associated virus (HUMAN GENE THERAPY 15:405-413.), and the phenomenon of lowering the gene transfer efficiency due to the immune response is less in the adenovirus than in the adeno-associated virus (World J Gastroenterol. 2016 Jan. 7; 22(1):326-37.).

The number of viruses for treatment can be represented by the number of viral particles including the vector genome or the number of infectable viruses. That is, since about 1% of the virus particles are the effective number of viruses that can actually be infected, IU (infection unit) or PFU (plaque forming unit) is used to indicate this.

The cell transformed by the vector can be bacteria.

The bacterium can be non-pathogenic or non-toxic, and can be *Listeria, Shigella, Salmonella*, or *E. coli*. By introducing the vector into bacteria, DNA of a gene included in the vector can be mass-replicated or proteins can be mass-produced.

The vector according to the present invention can be introduced into cells using a method known in the art. For example, transient transfection, microinjection, transduction, cell fusion, calcium phosphate precipitation, liposome-mediated transfection, DEAE dextran-mediated transfection, polybrene-mediated transfection, electroporation, gene gun, and other known methods for introducing nucleic acids into cells can be used to introduce the vector into cells, but not always limited thereto (Wu et al., J. Bio. Chem., 267: 963-967, 1992; Wu and Wu, J. Bio. Chem., 263:14621-14624, 1988).

In the case of the cells transformed with the vector containing the polynucleotide, it is preferably to contain $10^3$ to $10^8$ cells, and more preferably to contain $10^4$ to $10^7$ cells.

In preferred embodiments of the present invention, the present inventors confirmed that Runx3-BRD2 complex was formed 1 to 2 hours after serum stimulation in which BD1 of BRD2 was bound to the lysine residues 94 and 171 of the acetylated Runx3, BD2 was bound to the lysine residue 5 (H4K5-ac) of the acetylated histone 4, the lysine residue 12 (H4K12-ac) of histone 4 and the lysine residue 14 (H3K14-ac) of histone 3, and the binding of Runx3 and BRD2 was maintained for up to 8 hours in the presence of the CDK4 inhibitor (PD0332991) at the concentration of 11 nM known to be non-toxic to normal cells or the mTOR inhibitor (rapamycin) at the concentration of 100 nM known to be non-cytotoxic to normal cells. The present inventors also confirmed that the cancer apoptotic effect was significantly increased when the CDK4 inhibitor or mTOR inhibitor was administered simultaneously with Runx3 than when Runx3 was administered alone to Runx3 deficient cancer cells.

Therefore, the CDK4 inhibitor or mTOR inhibitor of the present invention can be effectively used for preventing or treating cancer by administering the same in combination with Runx3 protein.

Hereinafter, the present invention will be described in detail by the following examples and experimental examples.

However, the following examples and experimental examples are only for illustrating the present invention, and the contents of the present invention are not limited thereto.

Experimental Methods

1. Cell Line Preparation

HEK293 cells (ATCC, Manassas, VA, USA) were maintained in DMEM medium (Gibco BRL, Thermo Fisher Scientific, MA, USA, MA) supplemented with 10% fetal bovine serum (Gibco BRL) and 1% penicillin/streptomycin (Invitrogen, Carlsbad, CA, USA).

H460 cells (ATCC, Manassas, VA, USA) and H460 stable cells were maintained in RPMI 1640 medium (Gibco BRL) supplemented with 10% fetal bovine serum (Gibco BRL) and 1% penicillin/streptomycin (Invitrogen). All the cell lines were cultured in a 37° C., 5% $CO_2$ incubator.

2. Antibody

The antibody targeting RUNX3 (5G4) (Cat #ab40278) was obtained from Abcam (Cambridge, UK), and the antibody was diluted 1:3000. BRD2 (M01; 1:1000; Cat #H00006046-M01, Abnova, Taipei City, Taiwan) was used for immunoblotting and immunoprecipitation.

3. DNA Transfection, Immunoprecipitation (IP) and Immunoblotting (IB)

Transient transfection was performed in all cell lines using lipofectamine plus reagent and lipofectamine (Invitrogen). Cell lysates were incubated with an appropriate monoclonal or polyclonal antibody (2 μg of antibody/500 μg of lysate sample) at 4° C. for 3 hours, followed by incubation with protein G-Sepharose beads (Amersham Pharmacia Biotech, Piscataway, NJ, USA). For the detection of endogenous proteins at 4° C. for 1 hour, the lysate was incubated with an appropriate monoclonal or polyclonal antibody (1:1000~1:3000) at 4° C. for 6 to 12 hours, and then protein G-Sepharose beads (Amersham Pharmacia Biotech) were heated at 4° C. for 3 hours. The immune precipitate was digested on an SDS-polyacrylamide gel electrophoresis (SDS-PAGE) gel and transferred to a PVDF membrane (Millipore, Billerica, MA, USA). The membrane was blocked, immunoblotted with an appropriate antibody, treated with ECL solution (Amersham Pharmacia Biotech), and visualized in Amersham™ Imager 600 (GE Healthcare, Chicago, IL, USA).

4. Inhibitors and siRNA

CDK4 inhibitor (PD0332991), JNK inhibitor (JNK-IN-8), MEK1 inhibitor (U0126), p38 MAPK inhibitor (SB203580) and rapamycin (R8781) were purchased from Sigma-Aldrich. Cells were treated with CDK4 inhibitor (500 nM), JNK inhibitor (1 μM), MEK1 inhibitor (1 μM), p38 MAPK inhibitor (1 μM) or rapamycin (100 nM) and harvested at the designated time points after serum stimulation. Before serum starvation, a knockdown assay was performed by transfecting HEK293 cells with 50 nM siRNA using RNAiMAX (Invitrogen, CA, USA). Cells were harvested at the designated time points after serum stimulation. BRD2, p53, CDK4, RNF2 and Cyclin D1 siRNA were purchased from Bioneer (Daejeon, Korea). HDAC4 siRNA was purchased from Cell Signaling Technology. The sequence of siRNA is shown in Table 1 below.

TABLE 1

| Name | Sequence (5'->3') | SEQ. ID. NO: |
|---|---|---|
| si-BRD2 sense | CACUUGGCCUGCAU GACUA | SEQ. ID. NO: 1 |
| si-BRD2 antisense | UAGUCAUGCAGGCC AAGUG | SEQ. ID. NO: 2 |
| si-p53 sense | CAGUUUGAGGUGCG UGUU | SEQ. ID. NO: 3 |
| si-p53 antisense | AACACGCACCUCAA AGCUG | SEQ. ID. NO: 4 |
| si-CDK4 sense | CCAGAAUCUACAGC UACCA | SEQ. ID. NO: 5 |
| si-CDK4 antisense | UGGUAGCUGUAGAU UCCUGG | SEQ. ID. NO: 6 |
| si-Cyclin D1 sense | GACCUUCGUUGCCC UCUGU | SEQ. ID. NO: 7 |
| si-Cyclin D1 antisense | ACAGAGGGCAACGA AGGUC | SEQ. ID. NO: 8 |
| si-RNF2 sense | UGAUAGGGUAUUGA GUGUA | SEQ. ID. NO: 9 |
| si-RNF2 antisense | UACACUCAAUACCC UAUCA | SEQ. ID. NO: 10 |

5. Flow Cytometry

Cells were harvested and processed using FITC-Annexin V Apoptosis Detection Kit I (BD Biosciences, San Jose, CA, USA) and propidium iodide DNA staining protocol. Apoptosis and cell cycle were analyzed by flow cytometry on a BD FACS caliber machine (BD Biosciences). All data were analyzed using FlowJo software (https://www.flowjo.com).

Experimental Example 1: Confirmation of SWI/SNF and TFIID Invoked by Runx3-BRD2 Nucleosome Complex Determination of the restriction point is made 3 to 4 hours after serum stimulation. It has been disclosed that Runx3-BRD2 complex is formed 1 to 2 hours after serum stimulation, and this complex contributes to the R-point determination by regulating hundreds of genes (Chi, X. Z. et al. Runx3 plays a critical role in restriction-point and defense against cellular transformation. Oncogene 36, 6884-6894 (2017).). BRD2 contains two bromodomains (BD1 and BD2), each of which interacts with a unique protein. The interaction between Runx3 protein and other proteins was confirmed as follows after mitogenic stimulation.

As shown in FIG. 1a, BD1 was bound to the lysine residues 94 and 171 of the acetylated Runx3, BD2 was bound to the lysine residue 5 (H4K5-ac) of the acetylated histone 4, the lysine residue 12 (H4K12-ac) of histone 4 and the lysine residue 14 (H3K14-ac) of histone 3, and BRD2 was bound to SWI/SNF and TFIID through the C-terminal portion. In addition, RUNX3 was bound to these complexes through BRD2.

Figure 1B:
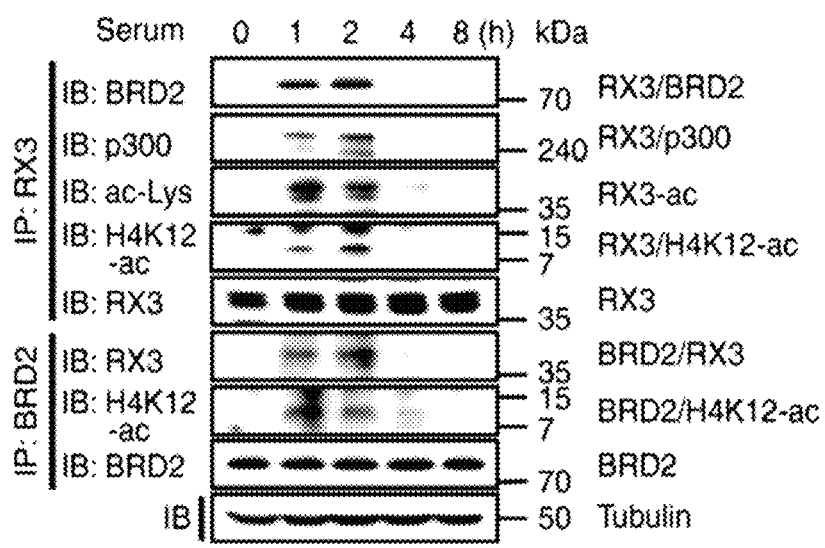
FIGS. 1b and 1c are diagrams illustrating the level of protein that formed a complex with Runx3 in HEK293 cells induced mitogenic stimulation by stimulation with 10% serum after serum depletion for 24 hours, measured by immunoprecipitation (IP) and immunoblotting (IB).

In particular, as shown in FIG. 1b, not only the interactions between BRD2, RUNX3, and the lysine 12 of the acetylated histone 4, but also the interactions between p300, Runx3 and the lysine 12 of the acetylated histone 4 were observed 1 to 2 hours after mitogenic stimulation. The interaction between RUNX3 and the lysine residue 12 of the acetylated histone 4 was significantly reduced due to the knockdown of BRD2.

The above results indicate that RUNX3 guided p300 to the target locus before the R-point, which acetylated histones, and that BRD2 was bound to both the acetylated RUNX3 and histones through two bromodomains.

Figure 1C:
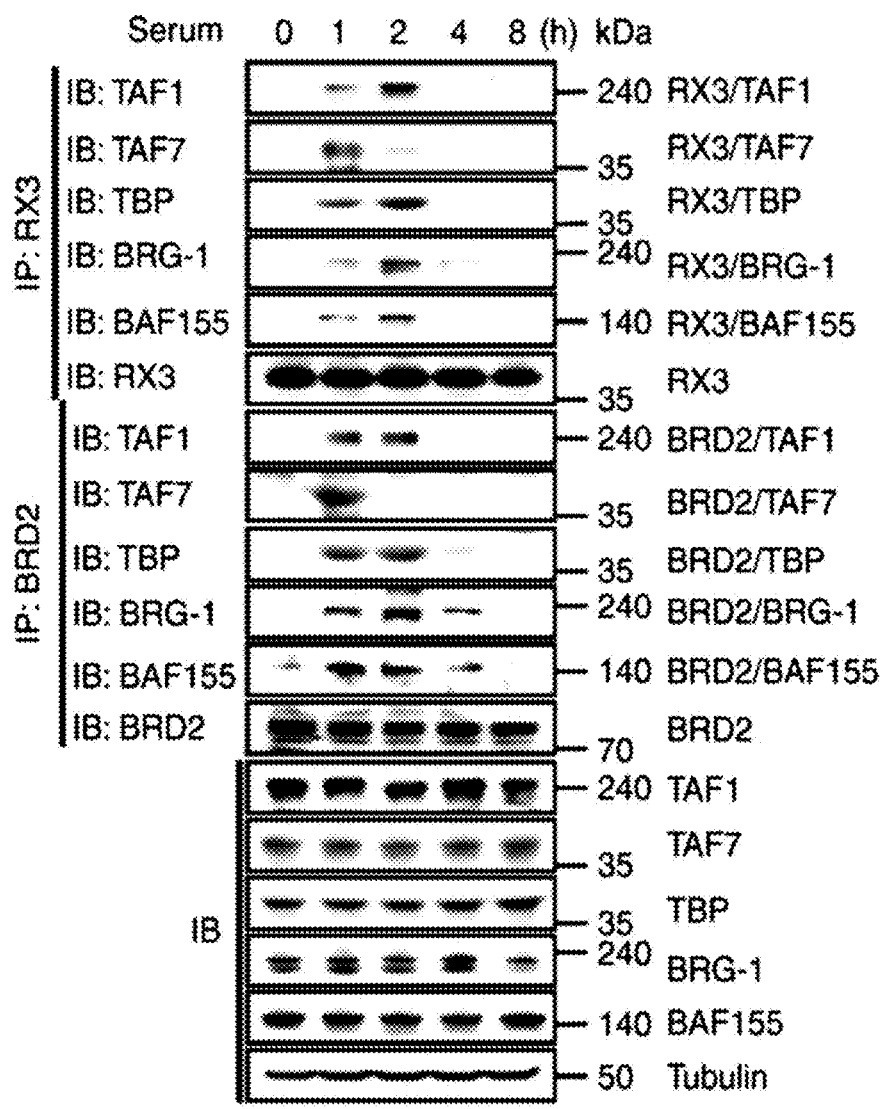

In addition, as shown in FIG. 1c, it was found that TAF1 (activated TAF1), TAF7 (suppressed TAF) and TBP formed a complex with BRD2 and RUNX3 1 hour after mitogenic stimulation. Thereafter, TAF7 was separated from the complex, and TFIID was activated after RUNX3-BRD2 binding. In addition, TAF1 and TBP were separated from RUNX3 4 hours after mitogenic stimulation. Similarly, BRG-1 and BAF155 (components of SWI/SNF complex) were also bound to RUNX3 and BRD2 1 to 2 hours after mitogenic stimulation and separated 4 hours after mitogenic stimulation. The binding of the RUNX3-BRD2 complex to the SWI/SNF and TFIID complex was confirmed through proximity ligation analysis (PLA).

The above results consistently suggest that the expression of the proteins related to R-point [p14ARF (hereinafter referred to as ARF), p53 and p21] was induced at the same time as when RUNX3 was bound to BRD2, SWI/SNF and TFIID.

The BRD2 knockdown experiment showed that the SWI/SNF and TFIID complex was bound to RUNX3 through BRD2. The above results suggest that the transient formation of the RUNX3-BRD2 complex was specific to the R-point.

Experimental Example 2: Confirmation of Formation of Rpa-RX3-TR by Binding of CDK4 and Cyclin D1

Figure 2A:
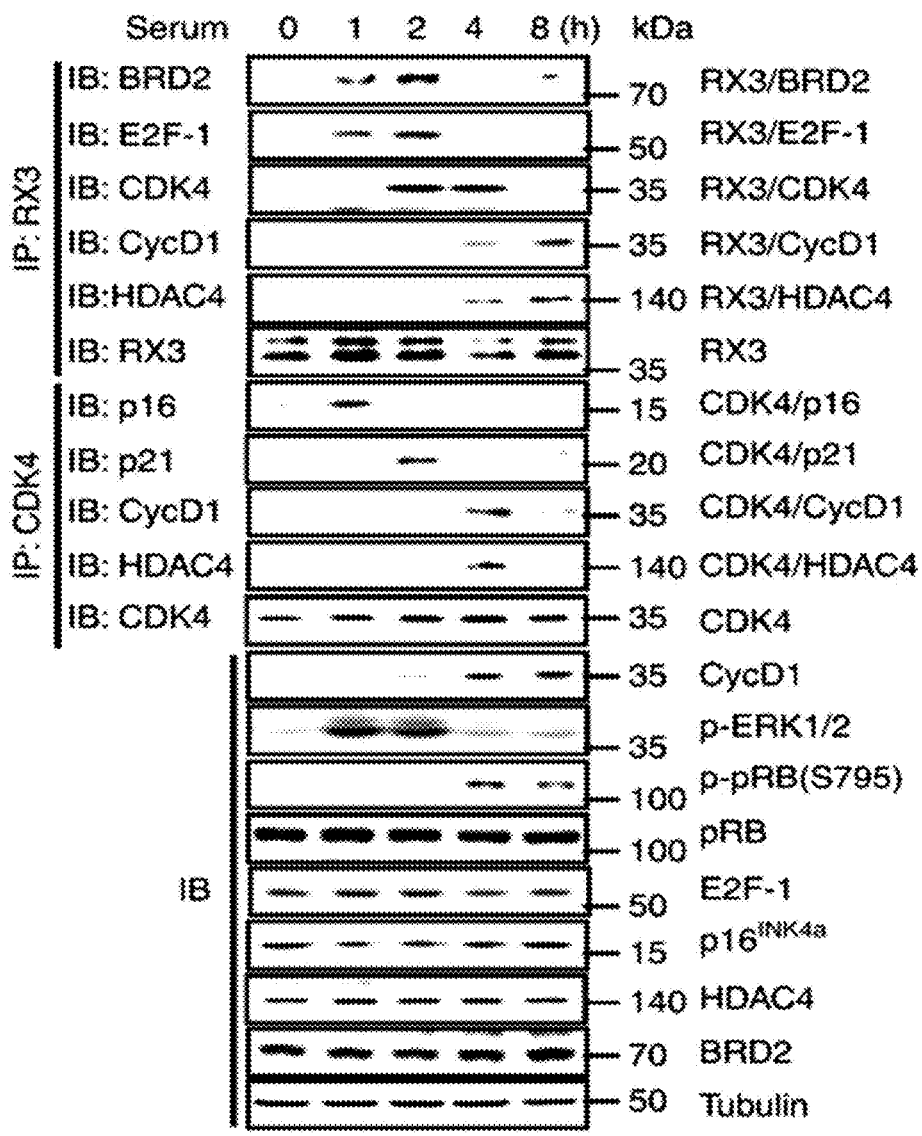
FIG. 2a is a diagram confirming that E2F1 was combined with RUNX3 by measuring the time-dependent formation of BRD2-RUNX3, E2F1-RUNX3, CDK4-RUNX3, Cyclin D1-RUNX3, HDAC4-RUNX3, p16INK4a-CDK4, p21-CDK4, Cyclin D1-CDK4 and HDAC4-CDK4 complexes by immunoprecipitation (IP) and immunoblotting (IB), and the time-dependent phosphorylation of pRB (at Ser-795) and ERK1/2 by immunoblotting (IB).
Figure 2B:
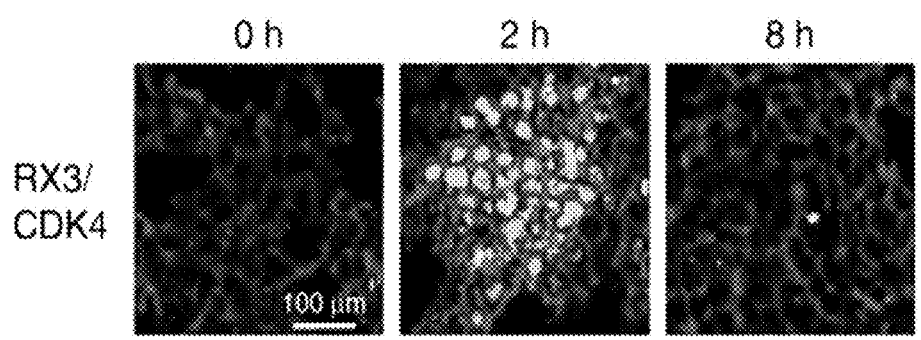
FIG. 2b is a diagram confirming the physical binding between RUNX3 and CDK4 through proximity ligation analysis (PLA) 2 hours after serum stimulation.

E2F1 was bound to RUNX3 1 to 2 hours after serum stimulation (FIG. 2a). When the $795^{th}$ serine of pRB was phosphorylated by Cyclin D1-CDK4/6, the pRB-E2F1 complex was released from RUNX3 (FIG. 2a). These results suggest that CDK4 approached Rpa-RX3-AC to phosphorylate pRB. Immunoprecipitation/immunoblotting analysis showed that CDK4 was bound to RUNX3 after 2 hours, and that the binding was then weakened (FIG. 2a). It was confirmed through proximity ligation analysis (PLA) that this physical binding between RUNX3 and CDK4 was visible 2 hours after serum stimulation (FIG. 2b). These results indicate that CDK4 was a component of Rpa-RX3-AC.

Figure 2C:
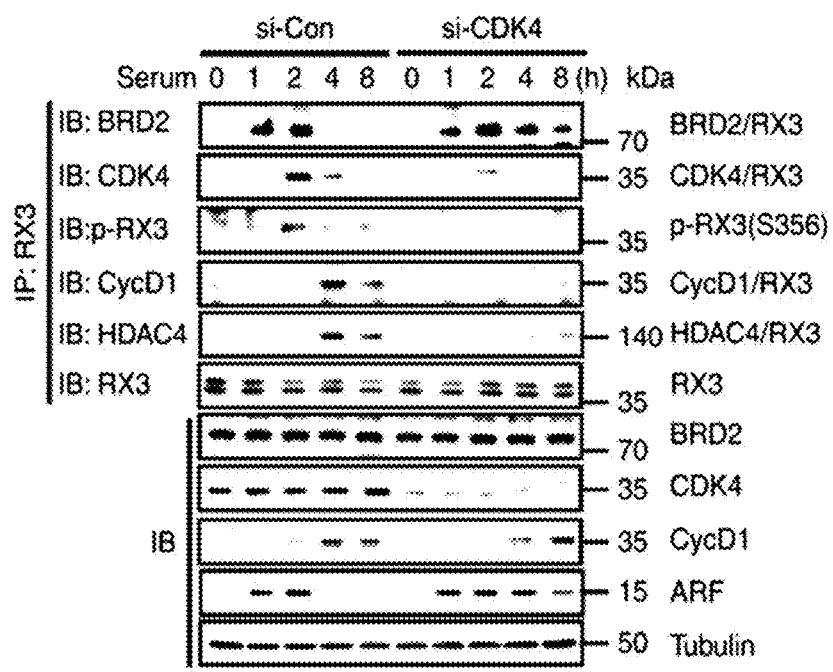
FIG. 2c is a diagram illustrating the time-dependent formation of BRD2-RUNX3, CDK4-RUNX3, HDAC4-RUNX3 and Cyclin D1-RUNX3 complexes in HEK293 cells treated with control or CDK4-specific siRNA (si-con or si-CDK4), and stimulated with serum after serum depletion for 24 hours, measured by immunoprecipitation (IP) and immunoblotting (IB). The time-dependent expression of ARF was measured by immunoblotting (IB), and it was confirmed that the knockdown of CDK4 significantly reduced the binding of RUNX3 to Cyclin D1 and HDAC4.

Although pRB and CDK4 were bound to Rpa-RX3-AC 2 hours after serum stimulation, the phosphorylation of pRB caused by CDK4 occurred 4 hours after stimulation (FIG. 2a). Through the analysis of the binding time between CDK4 and its binding proteins, it was confirmed that CDK4 was bound to p16 1 hour after stimulation, and then changed from p16 to p21 after 2 hours (FIG. 2a). P21 promotes the binding of Cyclin D1 to CDK4. However, Cyclin D1, which was expressed from 2 hours after stimulation, was bound to RNF2, but no CDK4 was bound to p21 at the same time (FIG. 2a). The Cyclin D1-CDK4 binding was observed after Rpa-RX3-TR was formed (4 hours after stimulation) (FIG. 2a). In particular, the knockdown of CDK4 significantly reduced the binding of RUNX3 to Cyclin D1 and HDAC4 (FIG. 2c). Therefore, the binding of RUNX3-BRD2 and the expression of ARF were maintained for up to 8 hours (FIG. 2c). These results suggest that CDK4 of Rpa-RX3-AC and Cyclin D1 of PRC1-Cyclin D1-HDAC4 provide docking sites for binding of two complexes capable of forming Rpa-RX3-TR.

Figure 3A:
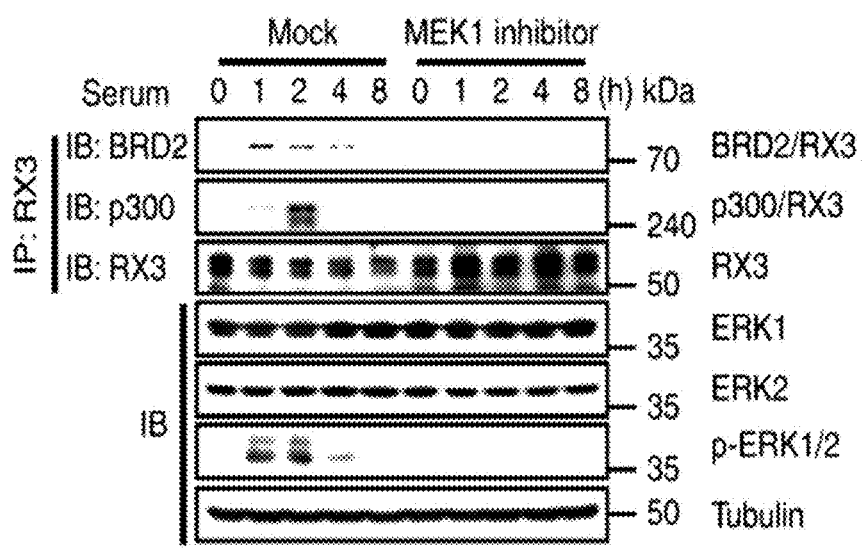
FIG. 3a is a diagram illustrating the time-dependent interaction of BRD2-RUNX3 and p300-RUNX3 as well as the phosphorylation of ERK1/2, measured by immunoprecipitation (IP) and immunoblotting (IB), confirming that the binding of BRD2-RUNX3 and p300-RUNX3 was eliminated by the treatment of the MEK1 inhibitor.

Experimental Example 3: Confirmation of Various Pathways Contributing to R-Point Transition The binding of BRD2-RUNX3 and p300-RUNX3 was inhibited by the treatment of a MEK1 inhibitor (FIG. 3a). The above results indicate that the RAS-MEK signaling pathway stimulated the formation of Rpa-RX3-AC.

Figure 3B:
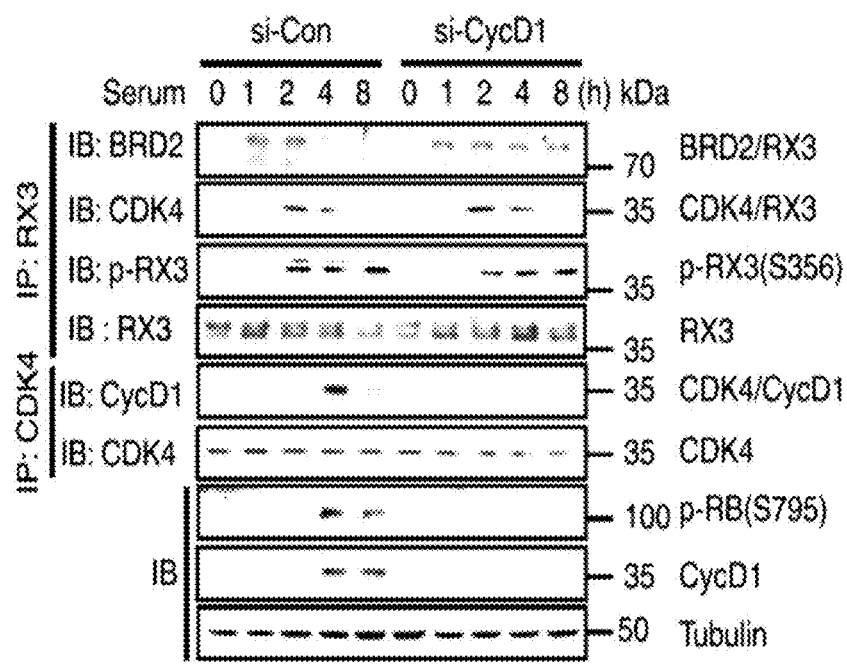
FIG. 3b is a diagram illustrating the time-dependent formation of BRD2-RUNX3 and CDK4-RUNX3 complexes and the phosphorylation of RUNX3 at Ser-356 and pRB at Ser-795, measured by immunoprecipitation (IP) and immunoblotting (IB), confirming that the knockdown of Cyclin D1 effectively reduced the phosphorylation of pRB (S795), but did not affect the phosphorylation of RUNX3 (S356).

The binding of Cyclin D1-CDK4 occurred 4 hours after serum stimulation, and the phosphorylation of pRB dependent on Cyclin D1-CDK4 also occurred at the same time (FIG. 2a). The knockdown of Cyclin D1 effectively reduced the phosphorylation of pRB (S795), but did not affect the phosphorylation of RUNX3 (S356) (FIG. 3b). These results suggest that CDK4 was activated independently of Cyclin D1 to promote the phosphorylation of RUNX3.

Figure 3C:
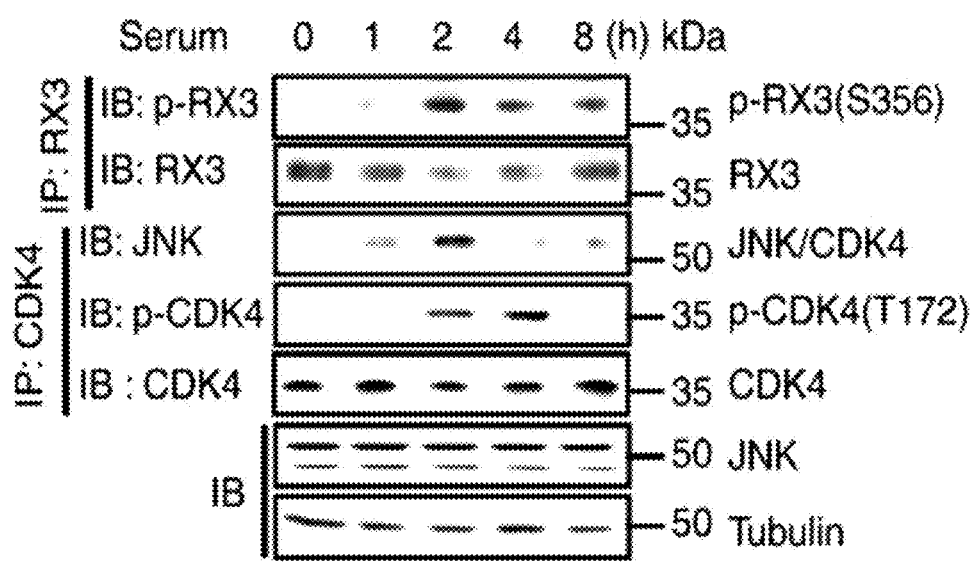
FIG. 3c is a diagram illustrating the time-dependent formation of JNK-CDK4 complex and the phosphorylation of RUNX3 at Ser-356 and CDK4 at Thr-172, measured by immunoprecipitation (IP) and immunoblotting (IB), confirming that JNK phosphorylated T172 of CDK4 2 hours after serum stimulation.
Figure 3D:
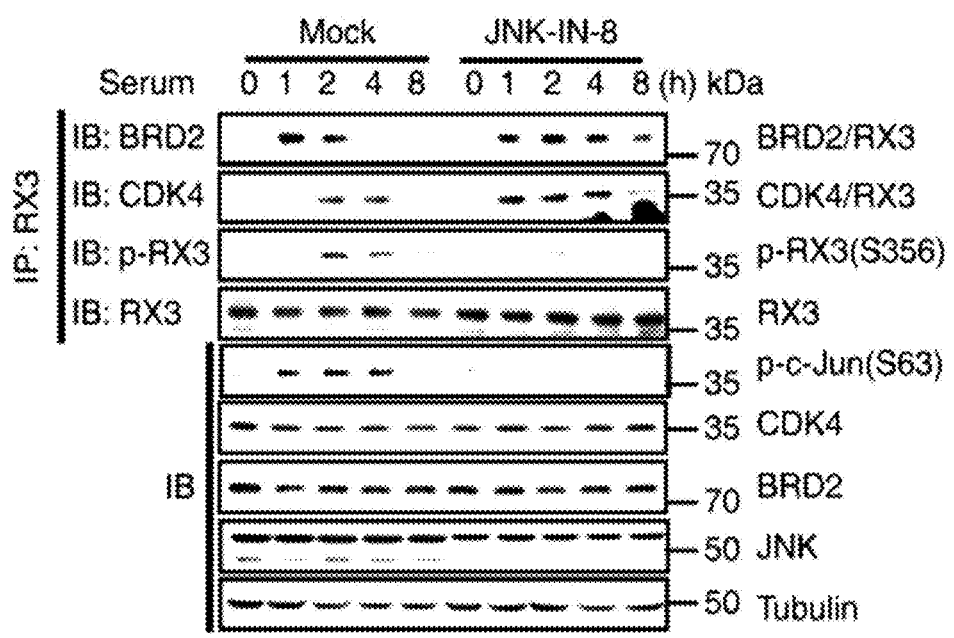
FIG. 3d is a diagram illustrating the time-dependent formation of BRD2-RUNX3 and RUNX3-CDK4 complexes in Ser-356 and the phosphorylation of RUNX3 measured by immunoprecipitation (IP) and immunoblotting (IB), and the time-dependent expression of ARF measured by immunoblotting (IB), confirming that the pharmacological inhibition of JNK activity remarkably reduced the phosphorylation of RUNX3 Ser-356 and maintained Rpa-RX3-AC for up to 8 hours.
Figure 3E:
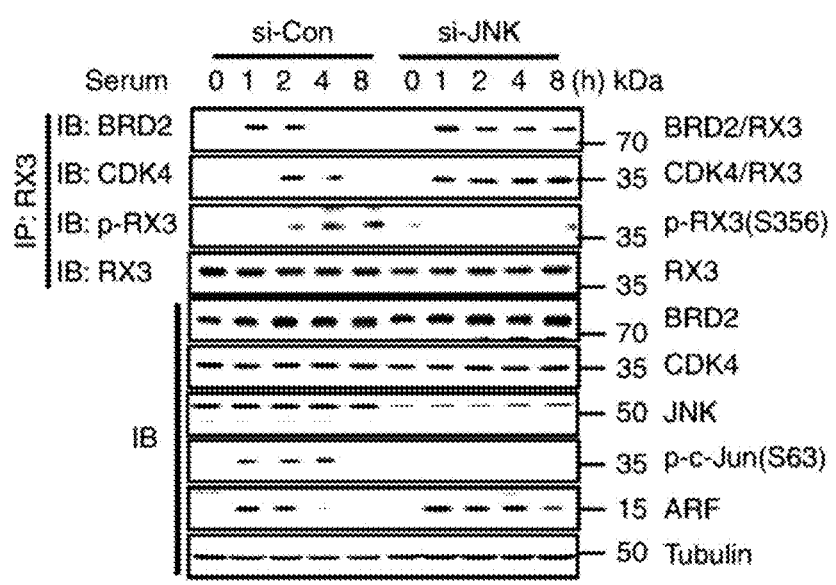
FIG. 3e is a diagram illustrating the time-dependent formation of BRD2-RUNX3 and CDK4-RUNX3 complexes in Ser-356 and the phosphorylation of RUNX3 measured by immunoprecipitation (IP) and immunoblotting (IB), and the time-dependent expression of ARF measured by immunoblotting (IB), confirming that the knockdown of JNK by siRNA also reduced the phosphorylation of RUNX3 Ser356 and maintained Rpa-RX3-AC.
Figure 3F:
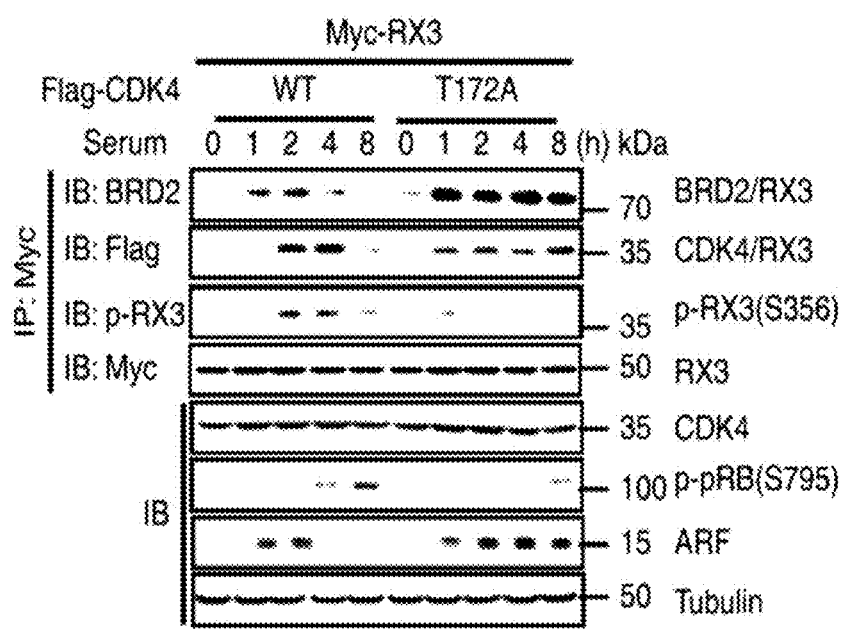
FIG. 3f is a diagram illustrating the time-dependent formation of BRD2-RUNX3 and CDK4-RUNX3 complexes in Ser-356 and the phosphorylation of RUNX3 measured by immunoprecipitation (IP) and immunoblotting (IB), and the time-dependent phosphorylation of pRB and the expression of ARF measured by immunoblotting (IB), confirming that the over-expressed CDK4-WT phosphorylated Myc-RUNX3 2-4 hours after serum stimulation, but Flag-CDK4-T172A (a mutant made to prevent phosphorylation by JNK) did not phosphorylate RUNX3 Ser356.

The activation of CDK4 depends on the activation of CDK-activating kinase (CAK). JNK has been known as one of CAKs that phosphorylate T172 of CDK4. It was found that JNK phosphorylated T172 of CDK4 2 hours after serum stimulation (FIG. 3c). The pharmacological inhibition of JNK activity remarkably reduced the phosphorylation of the $356^{th}$ serine of RUNX3 and maintained Rpa-RX3-AC for up to 8 hours (FIG. 3d). Similarly, the knockdown of JNK by siRNA also reduced the phosphorylation of the $356^{th}$ serine of RUNX3 and maintained Rpa-RX3-AC (FIG. 3e). The over-expressed CDK4-WT phosphorylated Myc-RUNX3 2 to 4 hours after serum stimulation. However, Flag-CDK4-T172A (a mutant made to prevent phosphorylation by JNK) did not phosphorylate the $356^{th}$ serine of RUNX3 (FIG. 3f). Flag-CDK4-T172A was bound to RUNX3 even earlier after serum stimulation and did not separate for a long time (FIG. 3f). Consistently, Flag-CDK4-T172A continued to maintain Rpa-RX3-AC and also extended the expression of ARF up to 8 hours (FIG. 3f). These results suggest that the JNK pathway also contributed to the R-point transition through the activation of CDK4.

Figure 3G:
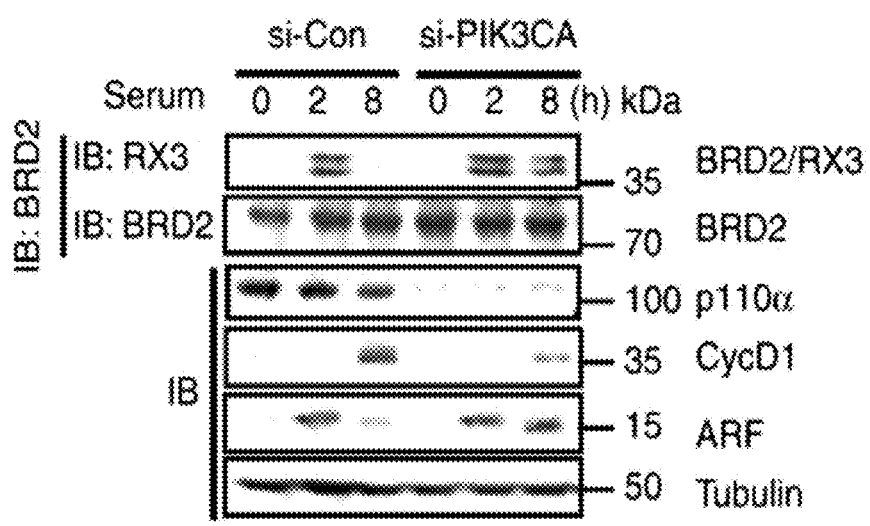
FIG. 3g is a diagram illustrating the time-dependent formation of BRD2-RUNX3 complex measured by immunoprecipitation (IP) and immunoblotting (IB), and the time-dependent expression of ARF measured by immunoblotting (IB), confirming that the knockdown of a PI3K catalytic subunit (PIK3CA, encoding p110a) reduced the level of Cyclin D1, maintained Rpa-RX3-AC, and extended the expression of ARF up to 8 hours.
Figure 3H:
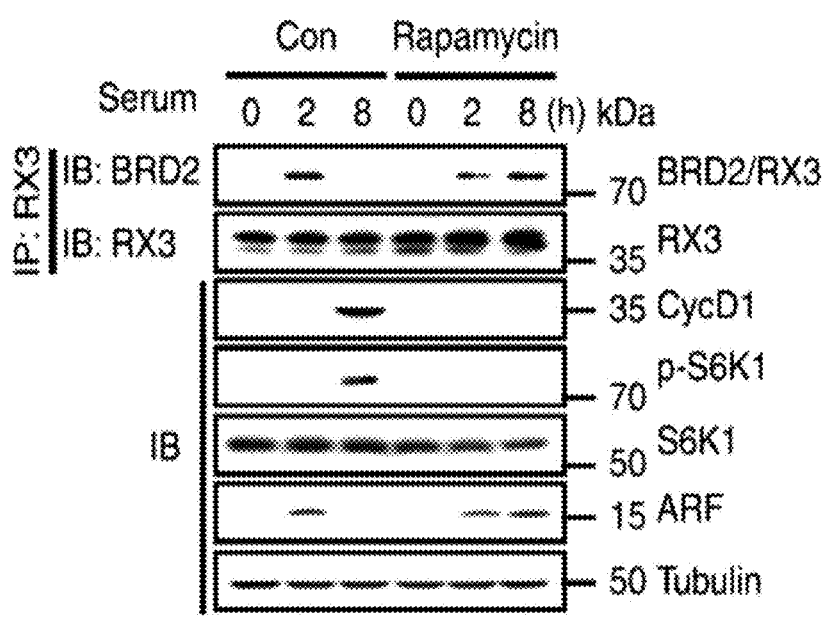
FIG. 3h is a diagram illustrating the time-dependent formation of BRD2-RUNX3 complex measured by immunoprecipitation (IP) and immunoblotting (IB), and the time-dependent expression of ARF measured by immunoblotting (IB), confirming that the ribosomal protein S6 kinase beta-1 (S6K1) phosphorylated by mTOR signaling was used for control.

It is known that the transcription and translation of Cyclin D1, which plays an important role in the formation of Rpa-RX3-TR, is stimulated through the respective RAS-RAF and RAS-PI3K pathways. As expected, the knockdown of a PI3K catalytic subunit (PIK3CA, encoding p110α) reduced the level of Cyclin D1, maintained Rpa-RX3-AC, and extended the expression of ARF up to 8 hours (FIG. 3g). The suppression of mTOR, a downstream effector of the RAS-PI3K-AKT pathway, using rapamycin, also maintained Rpa-RX3-AC and extended the expression of ARF up to 8 hours (FIG. 3h). These results suggest that the PI3K pathway also contributed to the conversion of Rpa-RX3-AC to Rpa-RX3-TR by inducing Cyclin D1.

Figure 4:
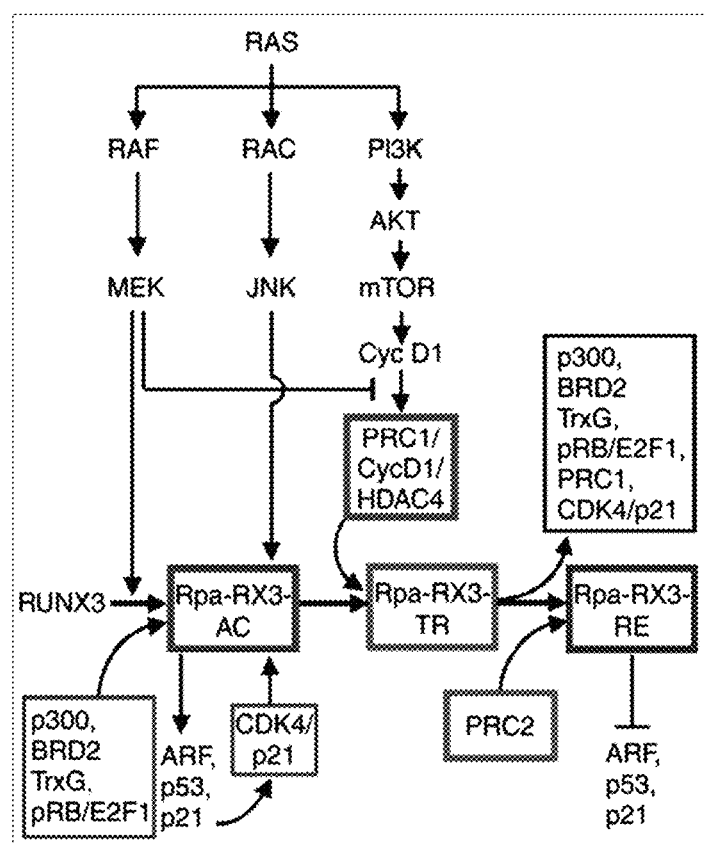
FIG. 4 is a schematic diagram illustrating the role of the RAS pathway in regulating the R-point transition, confirming that the RAS-RAF-MEK pathway promoted the formation of Rpa-RX3-AC and inhibited the formation of PRC1-Cyclin D1-HDAC4 complex, the RAS-RAC-JNK pathway activated CDK4 in Rpa-RX3-AC, and the RAS-PI3K pathway promoted the formation of Rpa-RX3-TR by contributing to the translation of Cyclin D1.

The above results suggest that the three major pathways downstream of RAS (MEK, JNK, and PI3K) contributed to the R-point conversion at a distinct stage. The contribution at each step to the R-point of these pathways is summarized in FIG. 4.

Experimental Example 4: Confirmation of Effect of Improving Stability of Runx3-Brd2 Complex by Treatment of CDK4 Inhibitor and mTOR Inhibitor Compounds in Cells In Experimental Examples 2 and 3, the main action points in the process of forming the Rpa-Rx3-TR complex from the Rpa-Rx3-AC complex and then converting to the Rpa-Rx3-

RE complex were the phosphorylation of Runx3 by CDK4, the binding of the phosphorylated Runx3 to cyclinD1, the PI3K-AKT-mTOR pathway, which activates cyclinD1, and the RAC-JNK pathway, another RAS pathway. Therefore, it was confirmed that the Rpa-Rx3-AC complex could be sustained by the treatment of a CDK4 inhibitor, mTOR inhibitor, or siRNA to inhibit protein synthesis of major pathways of action.

Accordingly, the present inventors predicted that the treatment of a CDK4 inhibitor (PD0332991) would increase the effect of sustaining the physical binding between Runx3 and BRD2, and performed the following experiment.

Particularly, the physical binding between Runx3 and Brd2 1 to 8 hours after serum stimulation was confirmed in an experiment treated with a CDK4 inhibitor at the concentration of 1 nM or more. In experiments not treated with a CDK4 inhibitor or treated with a CDK4 inhibitor at the concentration of 1 nM, the physical binding between Runx3 and Brd2 was not observed 8 hours after serum stimulation.

Figure 5:
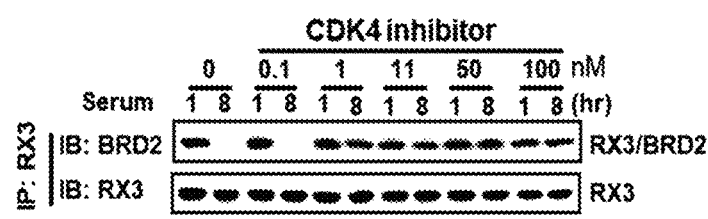
FIG. 5 is a diagram confirming that the binding of Runx3 and BRD2 was maintained for up to 8 hours when the CDK4 inhibitor (PD0332991) was present at the concentration of 11 nM known to be non-toxic to normal cells.

As a result, as shown in FIG. 5, it was confirmed that the binding of Runx3 and BRD2 was maintained for up to 8 hours when the CDK4 inhibitor (PD0332991) was present at the concentration of 11 nM known to be non-toxic to normal cells.

Figure 6:
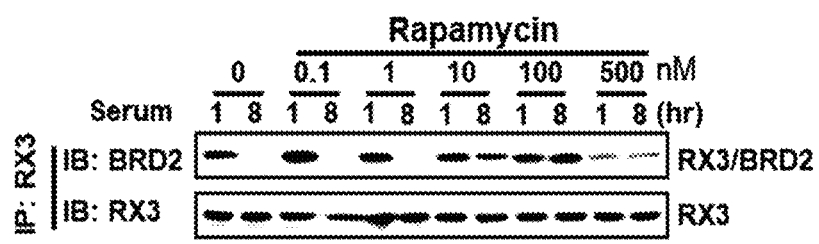
FIG. 6 is a diagram confirming that the binding of Runx3 and BRD2 was maintained for up to 8 hours when the mTOR inhibitor (rapamycin) was present at the concentration of 100 nM known to be non-cytotoxic to normal cells.

As shown in FIG. 6, it was also confirmed that the binding of Runx3 and BRD2 was maintained for up to 8 hours when the mTOR inhibitor (rapamycin) was present at the concentration of 100 nM known to be non-cytotoxic to normal cells.

Experimental Example 5: Confirmation of Cancer Apoptotic Effect by Co-Treatment of Runx3 Protein and CDK4 Inhibitor or mTOR Inhibitor Compound In Experimental Example 4, it was confirmed that the CDK4 inhibitor or the mTOR inhibitor compound increased the time for maintaining the Runx3-Brd2 complex. It was also confirmed that the cancer apoptotic effect was significantly increased when the CDK4 inhibitor or mTOR inhibitor was administered simultaneously with Runx3 than when Runx3 was administered alone.

Particularly, each cell line prepared in Experimental Methods 1 and 4 was harvested and processed using FITC-Annexin V Apoptosis Detection Kit I (BD Biosciences, San Jose, CA, USA) and propidium iodide DNA staining protocol. Apoptosis and cell cycle were analyzed by flow cytometry on a BD FACS caliber machine (BD Biosciences). All data were analyzed using FlowJo software (https://www.flowjo.com).

Figure 7A:
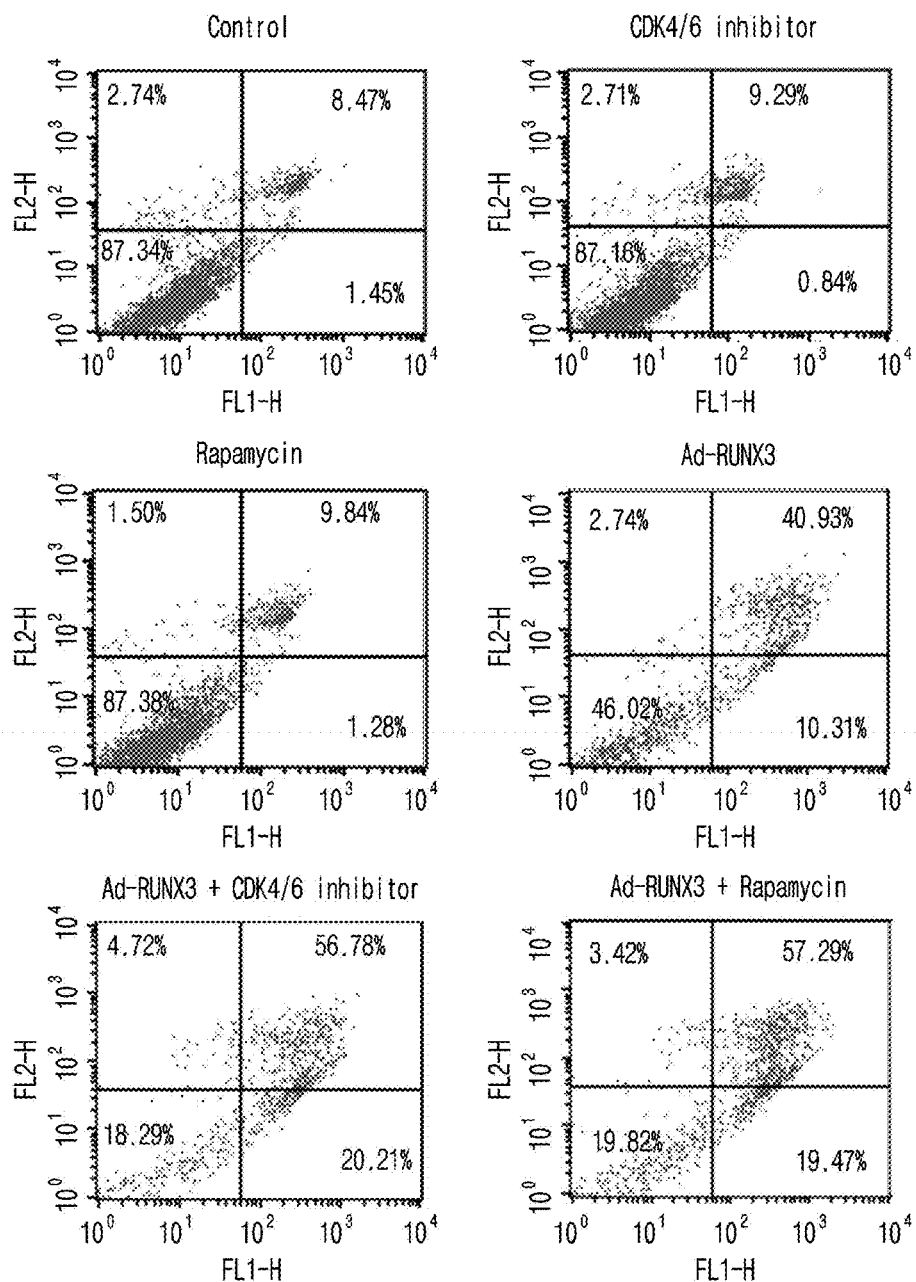
FIG. 7a is a diagram confirming the cancer apoptotic effect when Runx3 was introduced into Runx3 deficient H460 lung cancer cell line and when Runx3 and the CDK4 inhibitor were simultaneously introduced in the presence of the CDK4 inhibitor (PD0332991) at the concentration of 11 nM known to be non-toxic to normal cells, and the cancer apoptotic effect when Runx3 was introduced into Runx3 deficient cancer cells and when Runx3 and the CDK4 inhibitor were simultaneously introduced in the presence of the mTOR inhibitor (rapamycin) at the concentration of 100 nM known to be non-cytotoxic to normal cells.
Figure 7B:
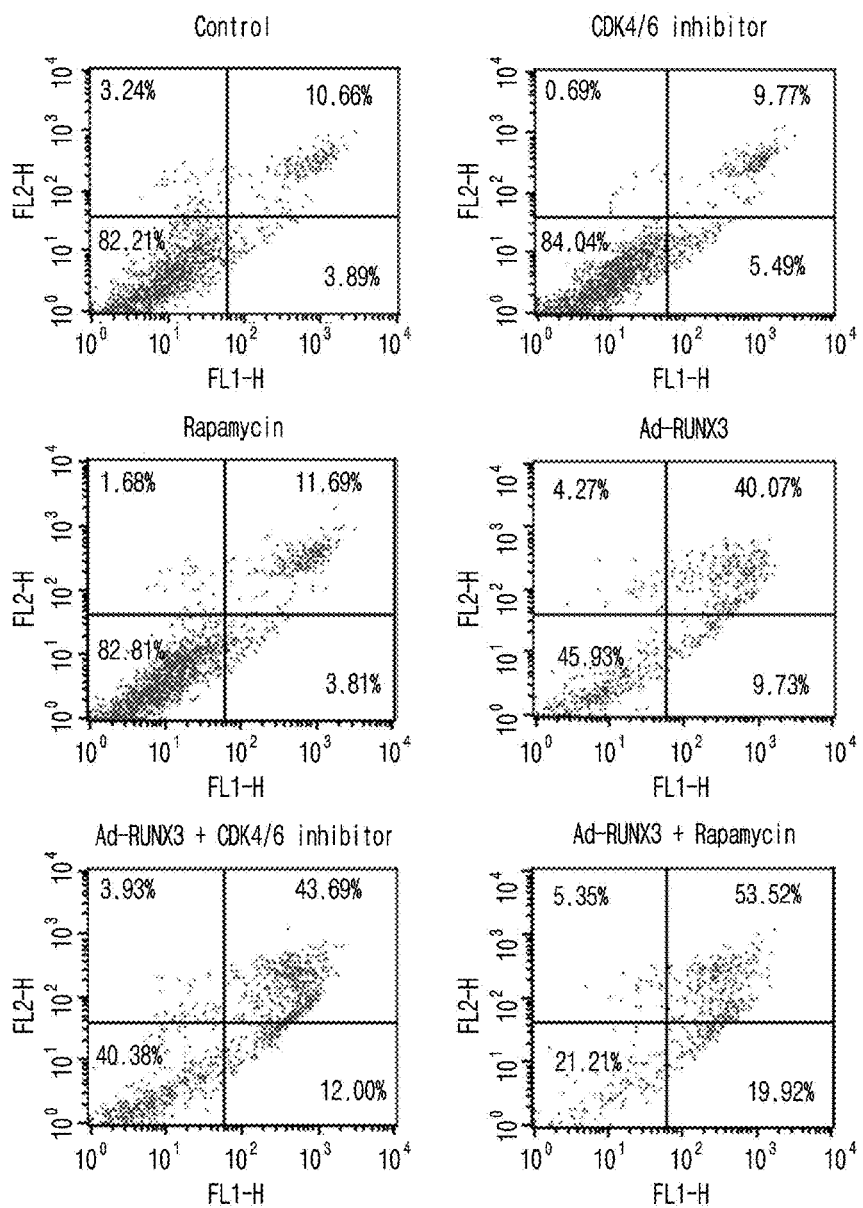
FIG. 7b is a diagram confirming the cancer apoptotic effect when Runx3 was introduced into Runx3 deficient MKN28 stomach cancer cell line and when Runx3 and the CDK4 inhibitor were simultaneously introduced in the presence of the CDK4 inhibitor (PD0332991) at the concentration of 11 nM known to be non-toxic to normal cells, and the cancer apoptotic effect when Runx3 was introduced into Runx3 deficient cancer cells and when Runx3 and the CDK4 inhibitor were simultaneously introduced in the presence of the mTOR inhibitor (rapamycin) at the concentration of 100 nM known to be non-cytotoxic to normal cells.
Figure 7C:
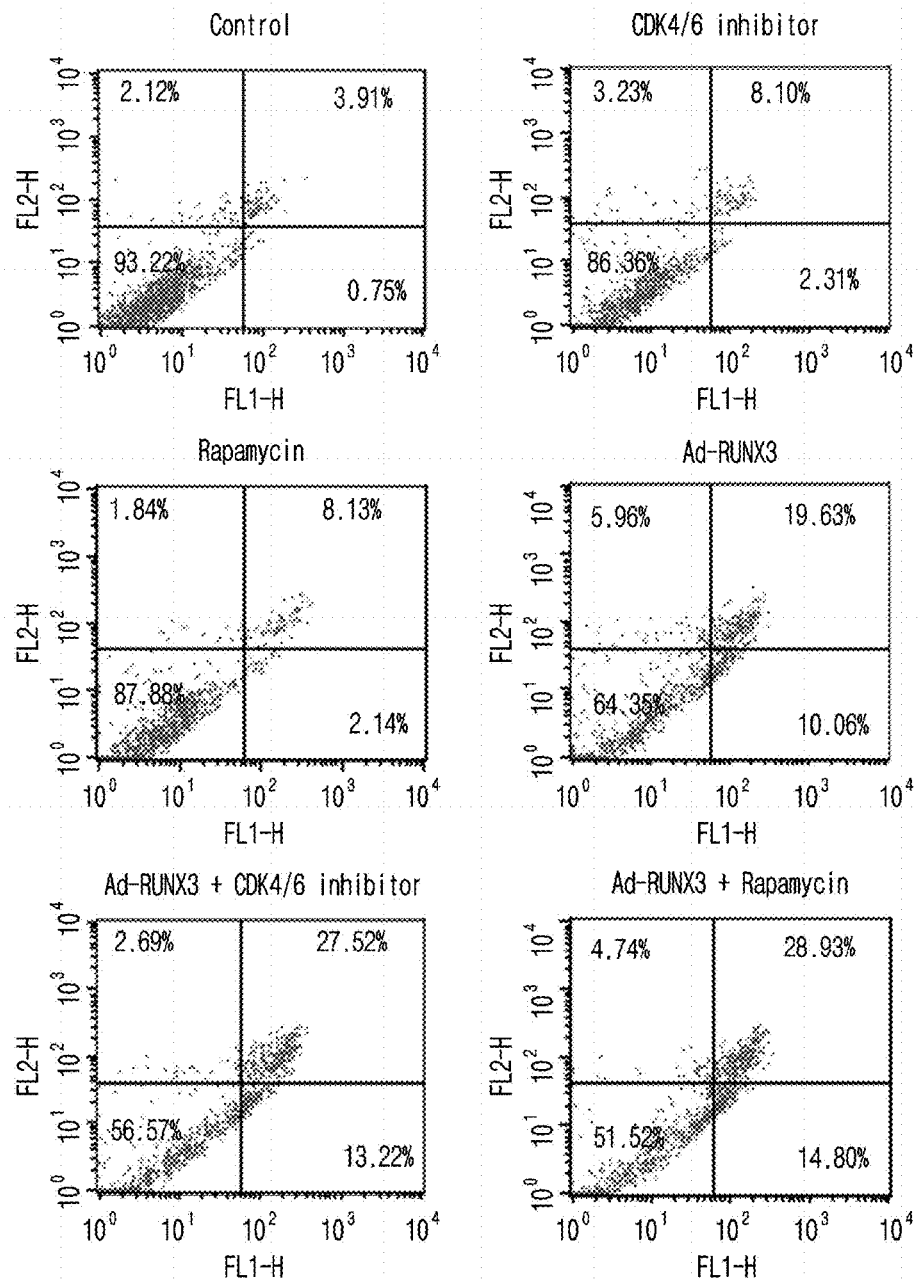
FIG. 7c is a diagram confirming the cancer apoptotic effect when Runx3 was introduced into Runx3 deficient PANC1 pancreatic cancer cell line and when Runx3 and the CDK4 inhibitor were simultaneously introduced in the presence of the CDK4 inhibitor (PD0332991) at the concentration of 11 nM known to be non-toxic to normal cells, and the cancer apoptotic effect when Runx3 was introduced into Runx3 deficient cancer cells and when Runx3 and the CDK4 inhibitor were simultaneously introduced in the presence of the mTOR inhibitor (rapamycin) at the concentration of 100 nM known to be non-cytotoxic to normal cells.

As a result, as shown in FIGS. 7a to 7c, it was confirmed that the cancer apoptotic effect when Runx3 was introduced into Runx3 deficient cancer cells and when Runx3 and the CDK4 inhibitor (PD0332991) were simultaneously introduced in the presence of the CDK4 inhibitor at the concentration of 11 nM known to be non-toxic to normal cells, and the cancer apoptotic effect when Runx3 was introduced into Runx3 deficient cancer cells and when Runx3 and the CDK4 inhibitor were simultaneously introduced in the presence of the mTOR inhibitor (rapamycin) at the concentration of 100 nM known to be non-cytotoxic to normal cells.

Figure 8:
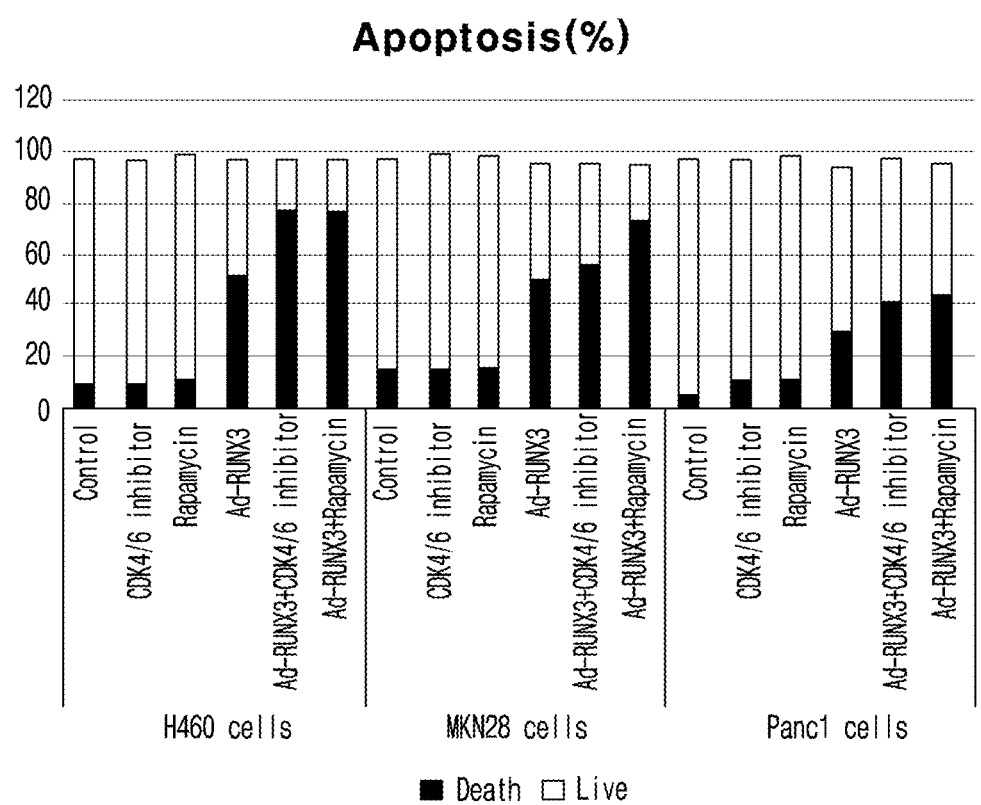
FIG. 8 is a diagram confirming that the cancer apoptotic effect was significantly increased in H460 lung cancer cell line, MKN28 stomach cancer cell line and PANC1 pancreatic cancer cell line when the adenovirus expressing Runx3 protein and the CDK4 inhibitor or the mTOR inhibitor were administered simultaneously than when the adenovirus expressing Runx3 protein was administered alone.

As shown in FIG. 8, it was also confirmed that the cancer apoptotic effect was significantly increased in H460 lung cancer cell line, MKN28 stomach cancer cell line and PANC1 pancreatic cancer cell line when the adenovirus expressing Runx3 protein and the CDK4 inhibitor or the mTOR inhibitor were administered simultaneously than when the adenovirus expressing Runx3 protein was administered alone. The above results suggest that the CDK4 inhibitor or mTOR inhibitor can be effectively used for treating cancer by administering the same in combination with Runx3.

The invention claimed is:

1. A method for treating K-Ras mutant non-small cell lung cancer in a subject in need thereof, comprising:
    administering a viral vector comprising a nucleic acid molecule encoding Runx3 (Runt-related transcription factor 3) at a therapeutically effective apoptotic amount for treating K-Ras non-small cell lung cancer, wherein the Runx3 comprises the amino acid sequence of SEQ ID NO: 11 or 12, in combination with administering a non-therapeutic, non-apoptotic amount of palbociclib at a concentration of 11 nM;
    wherein the therapeutically effective apoptotic amount of Runx3 leads to apoptosis of mutant K-Ras non-small cell lung cancer cells, and wherein said apoptosis is increased by the combination of the non-therapeutic, non-apoptotic amount of palbociclib at a concentration of 11 nM.

2. A method for treating K-Ras mutant non-small cell lung cancer in a subject in need thereof, comprising:
    administering a viral vector comprising a nucleic acid molecule encoding Runx3 (Runt-related transcription factor 3) at a therapeutically effective apoptotic amount for treating K-Ras non-small cell lung cancer, wherein the Runx3 comprises the amino acid sequence of SEQ ID NO: 11 or 12, in combination with administering a non-therapeutic, non-apoptotic amount of rapamycin at a concentration of 100 nM;
    wherein the therapeutically effective apoptotic amount of Runx3 leads to apoptosis of mutant K-Ras non-small cell lung cancer cells, and wherein said apoptosis is increased by the combination of the non-therapeutic, non-apoptotic amount of rapamycin at a concentration of 100 nM.

3. The method for treating lung cancer according to claim 1, wherein the viral vector is selected from a group consisting of retrovirus, adenovirus, herpes simplex virus and lentivirus.

4. The method for treating lung cancer according to claim 2, wherein the viral vector is selected from a group consisting of retrovirus, adenovirus, herpes simplex virus and lentivirus.

5. The method for treating lung cancer according to claim 1, wherein the viral vector is an adenovirus.

6. The method for treating lung cancer according to claim 2, wherein the viral vector is an adenovirus.

* * * * *